US011883208B2

(12) United States Patent
Agrawal et al.

(10) Patent No.: US 11,883,208 B2
(45) Date of Patent: Jan. 30, 2024

(54) MACHINE LEARNING-BASED SYSTEM FOR ESTIMATING GLUCOSE VALUES BASED ON BLOOD GLUCOSE MEASUREMENTS AND CONTEXTUAL ACTIVITY DATA

(71) Applicant: MEDTRONIC MINIMED, INC., Northridge, CA (US)

(72) Inventors: Pratik Agrawal, Porter Ranch, CA (US); Chantal M. McMahon, Atlanta, GA (US); Huzefa F. Neemuchwala, Simi Valley, CA (US); Yuxiang Zhong, Arcadia, CA (US); John Hoebing, Northridge, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 863 days.

(21) Appl. No.: 16/533,470

(22) Filed: Aug. 6, 2019

(65) Prior Publication Data
US 2021/0038163 A1 Feb. 11, 2021

(51) Int. Cl.
*A61B 5/00* (2006.01)
*A61B 5/11* (2006.01)
(Continued)

(52) U.S. Cl.
CPC .......... *A61B 5/7267* (2013.01); *A61B 5/1118* (2013.01); *A61B 5/14532* (2013.01);
(Continued)

(58) Field of Classification Search
CPC . A61B 5/7267; A61B 5/14532; A61B 5/4839; G16H 50/20; G16H 50/50; G16H 20/17
See application file for complete search history.

(56) References Cited

U.S. PATENT DOCUMENTS 4,562,751 A 1/1986 Nason et al.
4,685,903 A 8/1987 Cable et al.
(Continued)

FOREIGN PATENT DOCUMENTS

CN 114222597 A 3/2022
EP 2552313 A2 2/2013
(Continued)

OTHER PUBLICATIONS

Cooper Midroni, et al., Predicting Glycemia in Type 1 Diabetes Patients: Experiments With XGBoost, Nov. 3, 2016, Internationa;l Conference on Brain Inspired Cognitive Systems, Retrived From: https://www.researchgate.net/publication/328174513_Predicting_Glycemia_in_Type_1_Diabetes_Patients_Experiments_with_XGBoost/link/5f6cb55f299bf1b53eee1838/download.
(Continued)

*Primary Examiner* — Christian Jang
(74) *Attorney, Agent, or Firm* — Weaver Austin Villeneuve & Sampson LLP

(57) ABSTRACT

A method for estimating glucose values of a user and an insulin infusion and management system are provided. The insulin infusion and management system can include an insulin infusion device configured to deliver insulin to a user; a blood glucose meter; a source of user activity data; and a processor-based computing device that supports data communication with the insulin infusion device. A processor device of the computing device can perform a method for estimating glucose values of a user. In accordance with the
(Continued)

method, a first set of inputs can be received and processed via an estimation model for a user to generate a set of estimated glucose values that track actual glucose values.

20 Claims, 12 Drawing Sheets

(51) Int. Cl.
*A61B 5/145* (2006.01)
*G16H 50/20* (2018.01)
*G16H 50/50* (2018.01)
*G16H 20/17* (2018.01)

(52) U.S. Cl.
CPC .......... *A61B 5/4839* (2013.01); *A61B 5/4866* (2013.01); *A61B 5/7221* (2013.01); *G16H 50/20* (2018.01); *G16H 50/50* (2018.01); *A61B 5/0002* (2013.01); *G16H 20/17* (2018.01)

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,892,085 B2 | 5/2005 | McIvor et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,468,033 B2 | 12/2008 | Van et al. |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Stoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 10,307,109 B2 | 6/2019 | Randloev et al. |
| 2005/0043598 A1* | 2/2005 | Goode, Jr. ........... A61B 5/1473 600/347 |
| 2007/0123819 A1 | 5/2007 | Mernoe et al. |
| 2009/0299301 A1 | 12/2009 | Gottlieb et al. |
| 2010/0160861 A1 | 6/2010 | Causey, III et al. |
| 2011/0098548 A1 | 4/2011 | Budiman et al. |
| 2011/0160555 A1 | 6/2011 | Reifman et al. |
| 2014/0066889 A1 | 3/2014 | Grosman et al. |
| 2014/0163517 A1 | 6/2014 | Finan et al. |
| 2014/0304204 A1 | 10/2014 | Cameron et al. |
| 2016/0038673 A1* | 2/2016 | Morales ................. G16H 20/17 700/282 |
| 2016/0256629 A1* | 9/2016 | Grosman ........... A61B 5/14532 |
| 2017/0249445 A1 | 8/2017 | DeVries et al. |
| 2017/0252513 A1 | 9/2017 | Buck, Jr. et al. |
| 2017/0290535 A1 | 10/2017 | Rao et al. |
| 2018/0190375 A1* | 7/2018 | Chapela ................ G16H 50/30 |
| 2019/0043620 A1 | 2/2019 | Patek et al. |
| 2019/0069821 A1 | 3/2019 | Segman |
| 2020/0077931 A1 | 3/2020 | Goldner et al. |
| 2020/0196865 A1 | 6/2020 | Kamath et al. |
| 2020/0245913 A1 | 8/2020 | Dalal et al. |
| 2020/0375549 A1 | 12/2020 | Wexler et al. |
| 2021/0038163 A1 | 2/2021 | Agrawal et al. |
| 2021/0174949 A1 | 6/2021 | Gee et al. |
| 2021/0298648 A1 | 9/2021 | Hefner et al. |
| 2022/0039755 A1 | 2/2022 | Mikhno et al. |

(56) References Cited

U.S. PATENT DOCUMENTS

2022/0039756 A1 2/2022 Mikhno et al.
2023/0145330 A1 5/2023 Mikhno et al.

FOREIGN PATENT DOCUMENTS

EP 4010906 A1 6/2022
WO 2011119201 A2 9/2011

OTHER PUBLICATIONS

Ralph Ziegler, MD, et al., Intermittent Use of Continuous Glucose Monitoring: Expanding the Clinical Value of CGM, J Diabetes Sci Technol. May 2021; 15(3): 684-694. Published online Feb. 17, 2020.https://www.ncbi.nlm.nih.gov/bmc/articles/PMC8120049/ doi: 10.1177/1932296820905577.

Ashenafi Zebene Worldaregay, et al., Data-Driven Modeling and Prediction of Blood Glucose Dynamics: Machine Learning Applications in Type 1 Diabetes, Artificial Intelligence in Medicine, vol. 98, 2019, pp. 109-134, ISSN 0933-3657,https://www.sciencedirect.com/science/article/pii/S0933365717306218 https://doi.org/10.1016/j.artmed.2019.07.007.

Felicity Thomas, et al., A Simple Method to Model a Continuous Glucose Monitoring Signal, IFAC- PapersOnLineVolume 50, Issue 1, Jul. 2017, pp. 8775-8780https://www.sciencedirect.com/science/article/pii/S2405896317323479 https://doi.org/10.1016/j.ifacol.2017.08.1736.

International Preliminary Report on Patentability and Written Opinion of the International Searching Authority issued in corresponding application PCT/US2020/045293 dated Feb. 8, 2022 (8 pages).

International Preliminary Report on Patentability dated Oct. 6, 2022 in PCT Application No. PCT/US2021/015051.

International Search Report and Written Opinion dated Nov. 10, 2020, in Application No. PCT/US2020/045293.

International Search Report and Written Opinion dated May 17, 2021 in PCT Application No. PCT/US2021/015051.

U.S. Non-Final office Action dated Oct. 5, 2022 in U.S. Appl. No. 16/987,330.

U.S. Final Office Action dated Mar. 9, 2022, in U.S. Appl. No. 16/828,269.

U.S. Non-Final Office Action dated Oct. 27, 2021, in U.S. Appl. No. 16/828,269.

U.S. Non-Final office Action dated Oct. 19, 2022 in U.S. Appl. No. 17/178,087.

U.S. Non-Final Office Action dated May 24, 2023 in U.S. Appl. No. 18/150,493.

* cited by examiner

MACHINE LEARNING-BASED SYSTEM FOR ESTIMATING GLUCOSE VALUES BASED ON BLOOD GLUCOSE MEASUREMENTS AND CONTEXTUAL ACTIVITY DATA

TECHNICAL FIELD

Embodiments of the subject matter described herein relate generally to insulin delivery systems and, more specifically, to a machine learning-based system for estimating glucose values based on, for example, blood glucose measurements and contextual activity data.

BACKGROUND

Portable medical devices are useful for patients that have conditions that must be monitored on a continuous or frequent basis. For example, diabetics are usually required to modify and monitor their daily lifestyle to keep their blood glucose (BG) in balance. Individuals with Type 1 diabetes and some individuals with Type 2 diabetes use insulin (and other blood sugar lowering medications) to control their BG levels. To maintain glucose levels within a recommended range, patients with diabetes are advised to routinely keep strict schedules, including ingesting timely nutritious meals, partaking in exercise, monitoring BG levels daily, and adjusting and administering insulin dosages accordingly.

Infusion pump devices and insulin pump systems are relatively well known in the medical arts. Infusion pump devices and insulin systems are designed to deliver accurate and measured doses of insulin via infusion sets. An infusion set delivers the insulin to a patient through a small diameter tube that terminates at, e.g., a cannula inserted under the patient's skin. Use of infusion pump therapy has been increasing, especially for delivering insulin for diabetics.

In one type of system, the infusion pump can be programmed to inject insulin on a set schedule. For instance, a doctor or other healthcare administrator can program an insulin pump according to a set schedule so that it delivers insulin into the patient's bloodstream according to that schedule throughout the day. In addition, the patient can also simply activate the insulin pump to administer an insulin bolus as needed, for example, in response to the patient's high BG level. One drawback to this approach is that the user's lack knowledge of their blood glucose levels in any given point, and it is difficult for patients to determine when it may be necessary to administer insulin outside their scheduled administrations.

To address this problem, a patient can monitor BG levels using a BG meter or measurement device. For instance, a patient can utilize a blood glucose meter to intermittently measure their instantaneous blood sugar levels at any given time via a "finger prick test." Information from that measurement can be processed and used to determine whether insulin should be administered to regulate the patient's blood sugar level. A problem with this approach is that monitoring of blood glucose levels and the administration of insulin is done by the user on an ad hoc basis based on when they think insulin should be administered. This can be problematic in certain situations, such as with patients who experience hypoglycemia unawareness, which is a condition that can occur where a patient cannot perceive symptoms that might be indicators that their blood sugar is low.

To address this issue, continuous glucose monitoring systems can be used to help diabetic patients continuously monitor their blood glucose levels. Continuous glucose monitoring systems employ a continuous glucose sensor to monitor a patient's blood glucose level in a substantially continuous and autonomous manner. In many cases, a continuous glucose monitoring sensor is utilized in conjunction with an insulin infusion device or insulin pump as parts of a digital diabetes management system. The digital diabetes management system can determine the amount of glucose in the patient's blood at any given time so that an appropriate amount of insulin can be automatically administered to help regulate the amount of glucose in the patient's blood. This way insulin can be automatically administered depending on the patient's specific needs such that their blood sugar levels do not go too high or too low at any particular time. This way, an equilibrium or balance can be achieved between entry of glucose into the body (e.g., the amount of glucose that is being introduced into the patient's blood stream via meals) and how much glucose is being consumed or utilized by the patient.

While existing continuous glucose monitoring systems that employ a continuous glucose sensor work well, such continuous glucose monitoring systems are often too expensive for potential users to afford. In some cases, a patient's insurance does not cover such therapy or the patient's insurance may refuse to pay for the patient to use such a solution if the patient does not fall within a high enough risk category to be covered for such therapy. In addition, some patients may simply choose not to utilize continuous glucose monitoring systems for lifestyle reasons. For instance, a particular user may choose not to wear a continuous glucose monitor or sensor arrangement because it could be uncomfortable, or they choose not to wear it all the time for other reasons. This can prevent a large group of users from using a digital diabetes management solution.

Accordingly, it is desirable to provide digital diabetes management solutions that are less expensive and can thus be an option for users who are unable to afford more expensive continuous glucose monitoring systems. Furthermore, other desirable features and characteristics will become apparent from the subsequent detailed description and the appended claims, taken in conjunction with the accompanying drawings and the foregoing technical field and background.

BRIEF SUMMARY

A method for estimating glucose values of a user and an insulin infusion and management system are provided. The insulin infusion and management system can include an insulin infusion device configured to deliver insulin to a user; a blood glucose meter; a source of user activity data; and a processor-based computing device that supports data communication with the insulin infusion device. The computing device can include a processor device and a non-transitory processor-readable medium operatively associated with the processor device. The processor-readable medium comprises executable instructions configurable to cause the processor device to perform a method for estimating glucose values of a user. In one embodiment, the processor device is implemented at a backend server system, and the estimation model is executed as part of a web application at the backend server system. The backend server system is configured to communicate results of processing the estimated glucose values to one or more of a client device and an insulin infusion device. In another embodiment, the processor device is implemented at a client device, and the estimation model is executed as part of a mobile application at the client device. In another embodiment, the processor device is implemented at an insulin infusion device. In accordance with the method, a first set of inputs can be received and processed via an estimation model for a user to generate a set of estimated glucose values that track actual glucose values. The first set of inputs can comprise contextual activity data collected by a source of user activity data. For example, in one embodiment, the contextual activity data can include metabolic data about the user, and/or physical activity data about the user.

In one embodiment, the estimation model is an ensemble model that comprises one or more machine learning algorithms; and a physiological model. The machine learning algorithms can include one or more of: one or more artificial neural networks; one or more regression models; one or more decision tree models; one or more support vector machines; one or more Bayesian networks; one or more probabilistic machine learning models; one or more Gaussian processing models, one or more Hidden Markov models; and one or more deep learning networks.

In accordance with other embodiments, the estimation model can receive and process other information in addition to the first set of inputs to generate the set of estimated glucose values. For example, in accordance with another embodiment, the estimation model can also receive and process a second set of inputs comprising intermittent glucose measurements provided from a blood glucose meter to generate the set of estimated glucose values. In this embodiment, the processor device that executes the estimation model for the user processes the first set of inputs and the second set of user inputs to generate the set of estimated glucose values without using information from a continuous glucose sensor arrangement. In accordance with another embodiment, the estimation model can also receive and process a third set of inputs comprising nutritional information input by a user, and a fourth set of inputs comprising insulin delivered by an insulin infusion device of the user to generate the set of estimated glucose values. In this embodiment, the processor device that executes the estimation model for the user processes the first set of inputs, the second set of inputs, the third set of inputs and the fourth set of inputs to generate the set of estimated glucose values.

In one embodiment, the processing system can regularly determine whether the estimated glucose values are within an acceptable accuracy range. When the estimated glucose values are not within the acceptable accuracy range, the processing system can cause a first notification that is perceptible to the user to be generated. When the estimated glucose values are within the acceptable accuracy range, the processing system can utilize the estimated glucose value for diabetes management including controlling delivery of insulin by an insulin infusion device based on the estimated glucose values.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
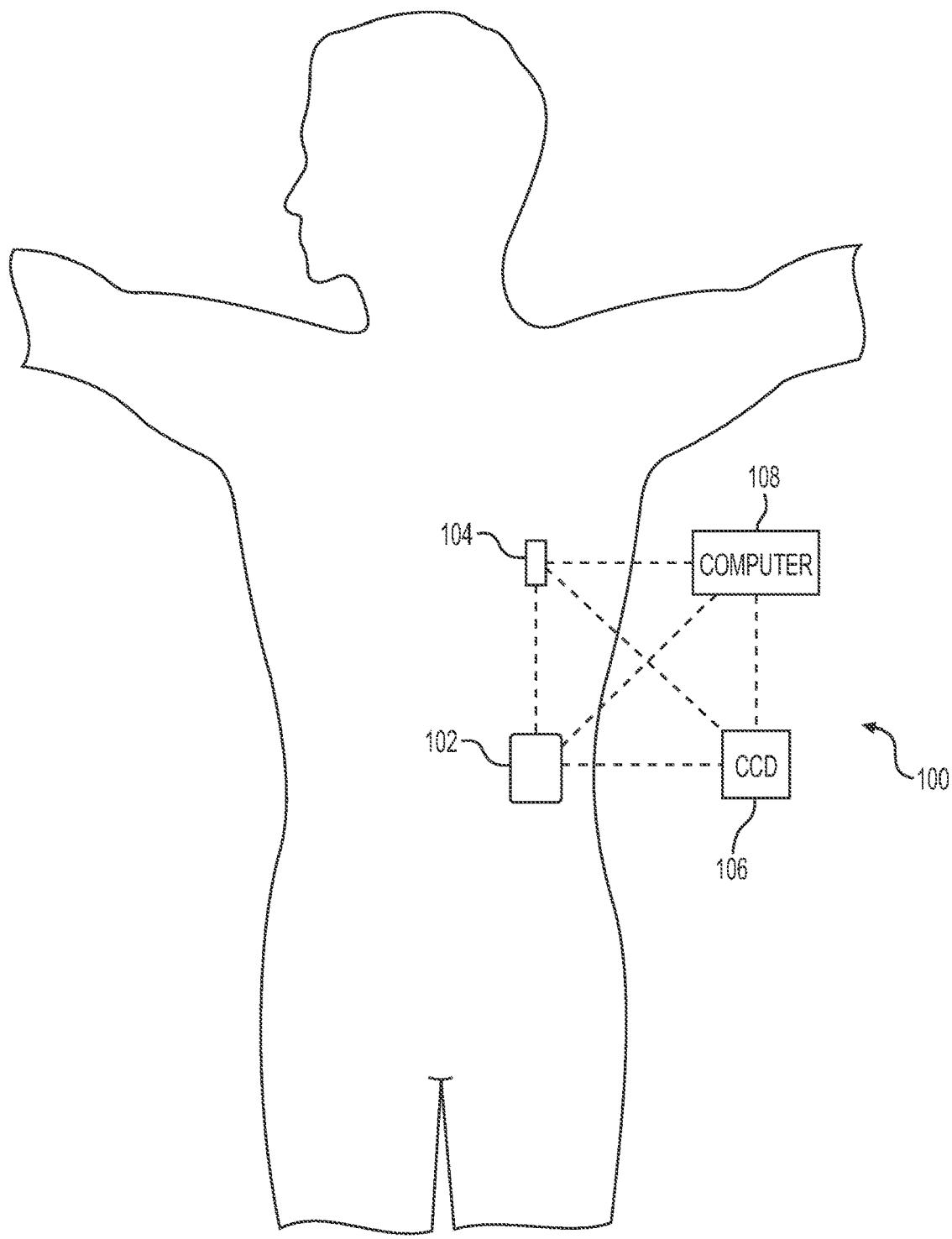
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate an insulin infusion device (or insulin pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos.: 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to linearly displace a plunger (or stopper) of a fluid reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop or automatic operating mode, dosage commands may be generated based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

In one non-limiting embodiment, a method and system are provided for estimating glucose values based, for example, on data from a BG meter and an activity tracker. In other embodiments, other contextual information, such as food (including carbohydrate and macronutrient intake) can also be used to estimate glucose values (e.g., to reconstruct continuous glucose data). Machine learning-based estimation/prediction models can be developed off-line for each patient, or updated online for continuous learning, particularly during retraining periods of CGM taking in current contextual data. Generic estimation/predication models can be built using patterns/instances from data collected from a similar cohort as the patient which provides a bigger data pool and hence larger scope for patient characterization. Because every person is different the estimation/prediction models are uniquely trained for each patient.

For example, a customized machine learning-based estimation/prediction model can be built for each patient during a training process using CGM data. The customized machine learning-based estimation/prediction model can then be invoked at run time based on finger-stick measurements entered by the user via a blood glucose meter in addition to other contextual information such as steps, heart rate, exercise, metabolic equivalents and other parameters collected from an activity tracker, and insulin and meal information from insulin pumps (or insulin pens) or user entries, while also taking into account their medical history and demographic information so that the predictions are not only personalized based on the individual's diabetes profile and behavior, but also equipped to account for deviations from a patient's regular routine. The customized machine learning-based estimation/prediction model can thus provide continuous current and predictive estimates of glucose levels in real-time using finger-stick measurements entered by the user via a blood glucose meter and including any of the other contextual information mentioned above. Also, because the contextual data for a patient can change over time, the estimation/prediction models can be updated on a regular basis. In other words, because a patient's condition can change over time, a patient can wear a continuous glucose sensor periodically (e.g., once or twice a month) to acquire data that can be used to retrain the estimation model so that it can generate more accurate estimates for that particular patient.

The functionality can reside, for example, both within a web-based application as well as a mobile application. The estimation models can be implemented/deployed at either a backend server that runs the estimation model as part of a web-based application and communicates information back to the user's phone, insulin pump or other end device, and/or can also implemented as part of a mobile application that runs on the user's phone or other end device and communicates information back to the insulin pump or other end device. The estimation models can also be implemented/deployed at an insulin pump. Regardless of the implementation, the applications can send push notifications to the patient to alert them in case of an estimated low or high excursion event, can receive requests from user and deliver precise, coherent answers, and can also provide a pathway for entering data which can be used to keep track of the user history as well as improve the prediction estimates.

The estimation model can be trained using a continuous glucose sensor device, and once it is trained and then personalized/tuned for a particular user/patient, the continuous glucose sensor does not need to be used on a regular basis. This can allow users/patients to rely less on a continuous glucose sensor. They only need to use a continuous glucose sensor periodically instead of on a regular basis.

Instead, a blood glucose meter can be used in conjunction with an activity tracker to generate inputs to the estimation model, and the estimation model can then generate estimated glucose values that approximate measured glucose values that would be measured by a continuous glucose sensor. In essence, the disclosed embodiments can allow a patient to use an activity tracker and intermittent measurements from a blood glucose meter without needing a continuous glucose sensor on a regular basis (e.g., the patient can use a continuous glucose sensor periodically for calibration, but then only use a blood glucose meter and an activity tracker in conjunction with an estimation model the remainder of the time).

In one embodiment, additional types of data can be processed by the estimation model, which can improve the accuracy of the estimates. For example, a patient can estimate their glucose values using meal data that describes what the patient has recently eaten, intermittent blood glucose measurements from a blood glucose meter (that are taken by a user, for example, via finger stick measurements), and other contextual activity data that is received on a continuous basis from an activity tracker or other source of activity information about the patient. This other contextual activity data can include data such as physical activity data (e.g., heart rate, number of steps, or metabolic equivalents, etc.), metabolic data (e.g., calories burned), etc. This information can be used via an estimation or predication module to estimate glucose values in a way that approximates, with high accuracy, blood glucose measurements that would be measured by a continuous glucose sensor without having to incur the cost of, or permanently attach, a continuous glucose sensor. When the estimated glucose values are accurate enough, they can be used, for example, to drive an insulin infusion device so that it administers insulin to a patient, or to provide notifications to a patient or health care partner to manually inject a bolus of insulin on an as needed basis depending on their estimated glucose values and other information such as activity data, meal information, etc., or alternatively to provide health care providers with information to adjust basal rate settings of an inulin infusion device so that they are appropriate for a particular patient to meet their needs. It may also be used as a medication titration advisor for individuals on other types of blood sugar lowering medications. When the estimated glucose values are not accurate enough, then this condition can be used to trigger a notification, warning, alarm or alert, for example, at another device such as at the insulin pump, the user's smartphone or other smart device, etc. to inform the user that they should not trust the system and to recommend that the user to wear another sensor (e.g., CGM) to retrain the estimation model.

Thus, the proposed method and system can provide a new digital diabetes management solution that is cheaper and more affordable; more likely to be used by users who are unable to afford digital diabetes management systems; more likely to be approved by insurance, etc. The proposed method and system can also help users start using a digital diabetes management solution until they transition to a CGM-based system for diabetes management.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos.: 6,088,608, 6,119,028, 6,589,229, 6,740,072, 6,827,702, 7,323,142, and 7,402,153 or U.S. Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
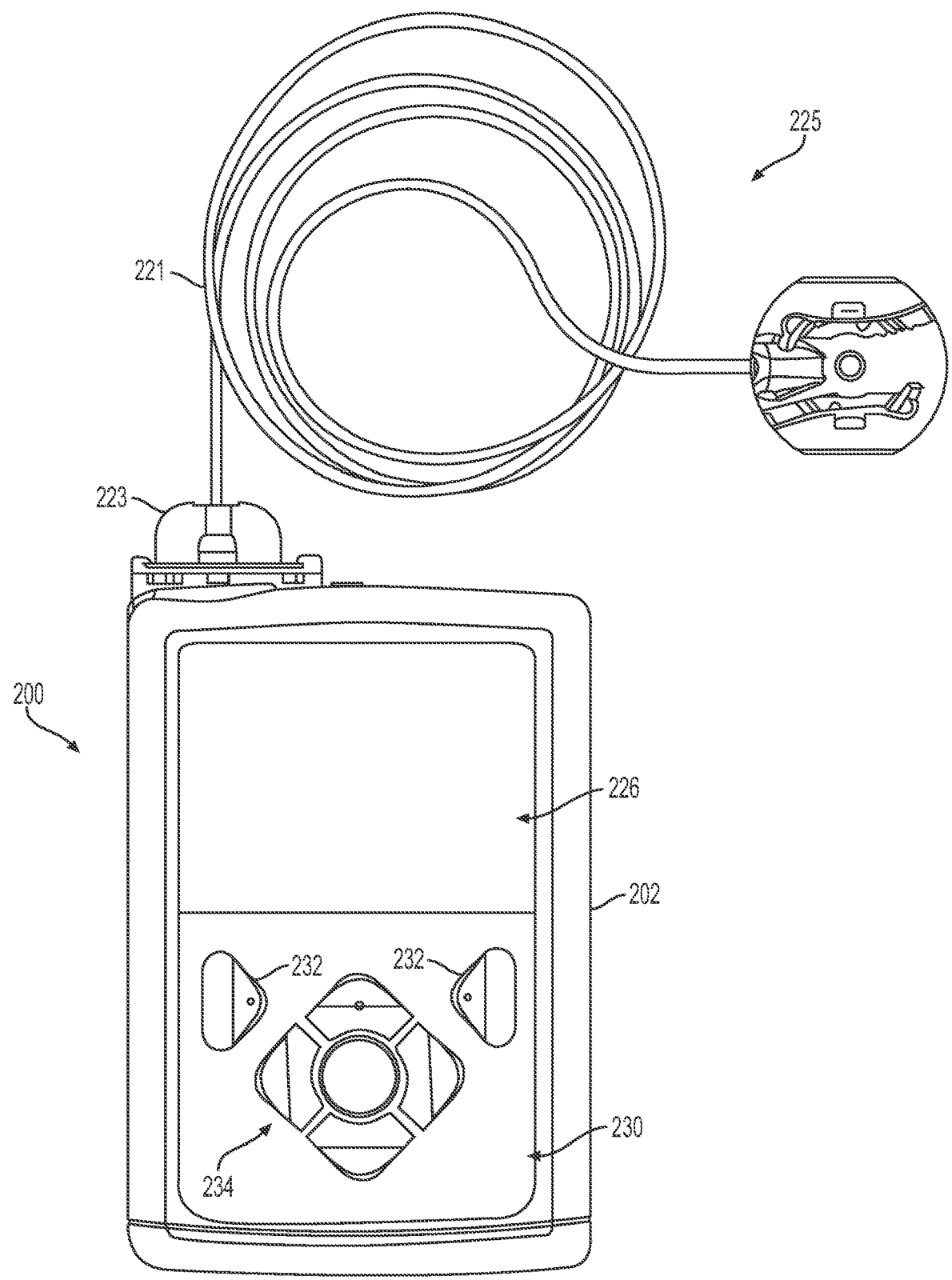
FIG. 2 depicts a plan view of an exemplary embodiment of a fluid infusion device suitable for use in the infusion system of FIG. 1.
Figure 3:
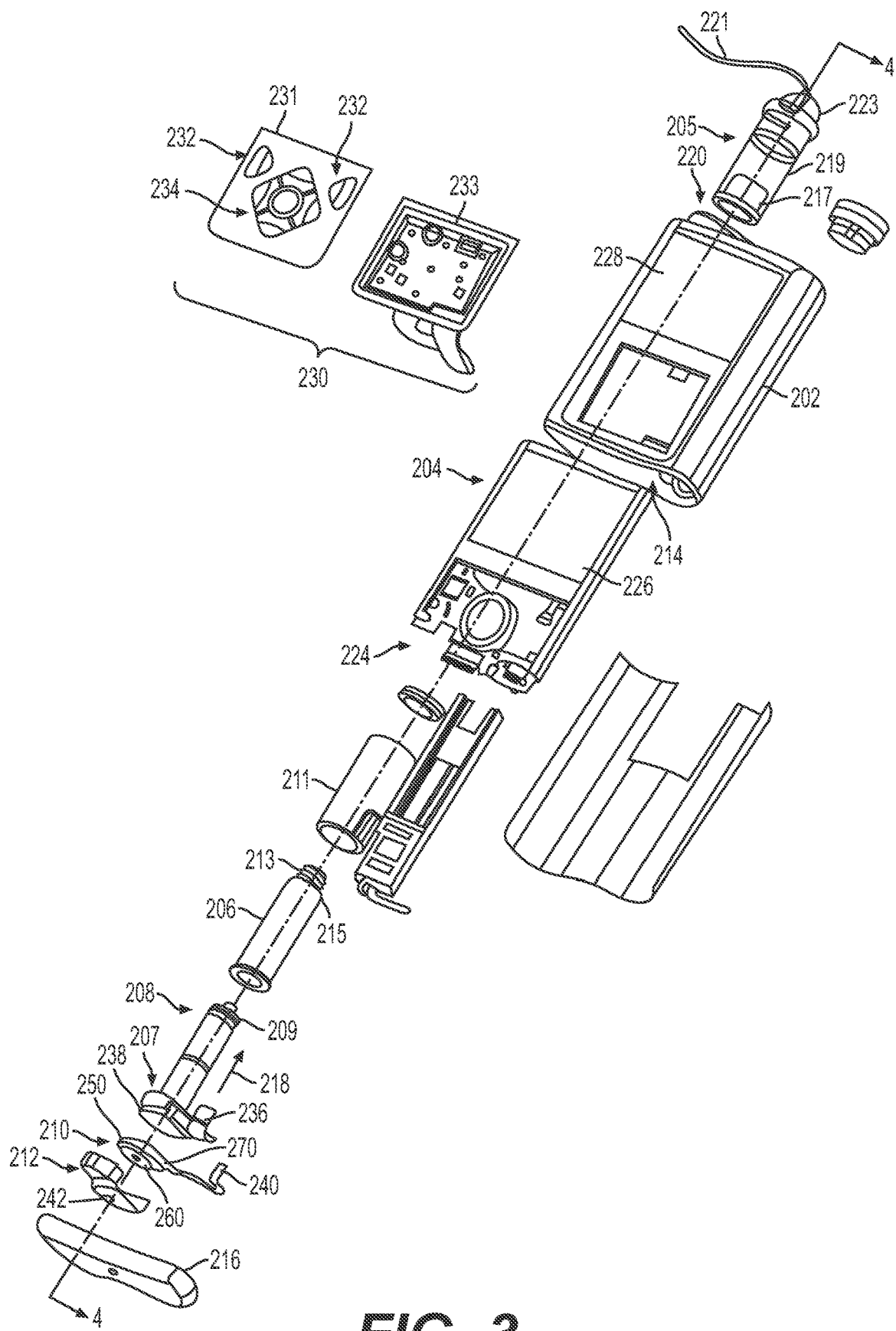
FIG. 3 is an exploded perspective view of the fluid infusion device of FIG. 2.
Figure 4:
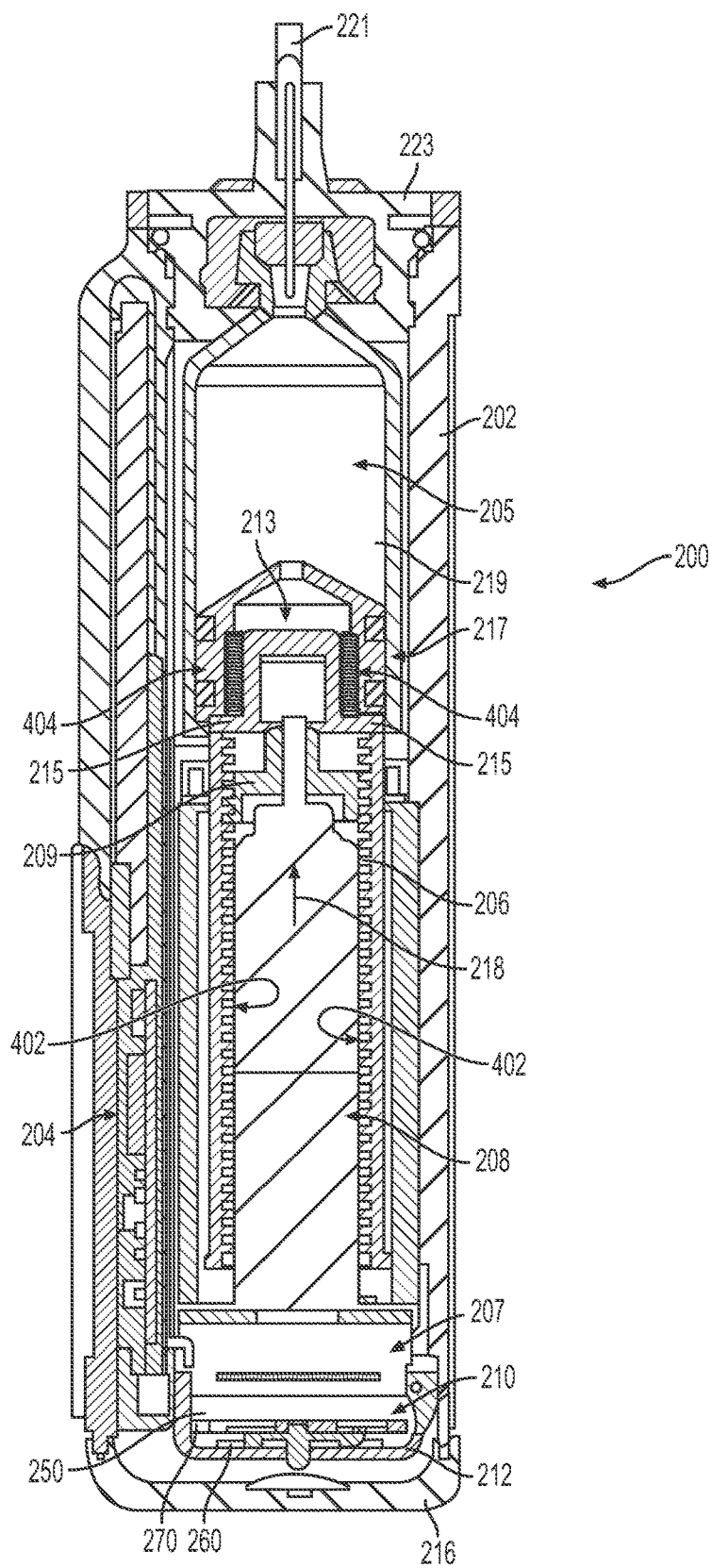
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion device 200 is subjected to shock or vibration; when the infusion device 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion device 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion device 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion device 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display element 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. The control electronics 224 is also suitably configured and designed to support various user interface, input/output, and display features of the fluid infusion device 200. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion device 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion device 200, for example, to administer a bolus of insulin, to change therapy settings, to change user preferences, to select display features, to set or disable alarms and reminders, and the like. In this regard, the control electronics 224 maintains and/or provides information to the display element 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display element 226 may be realized as a touch screen or touch-sensitive display, and in such embodiments, the features and/or functionality of the HMI elements 232, 234 may be integrated into the display element 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing capping member 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of the arrow that represents the axial direction 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
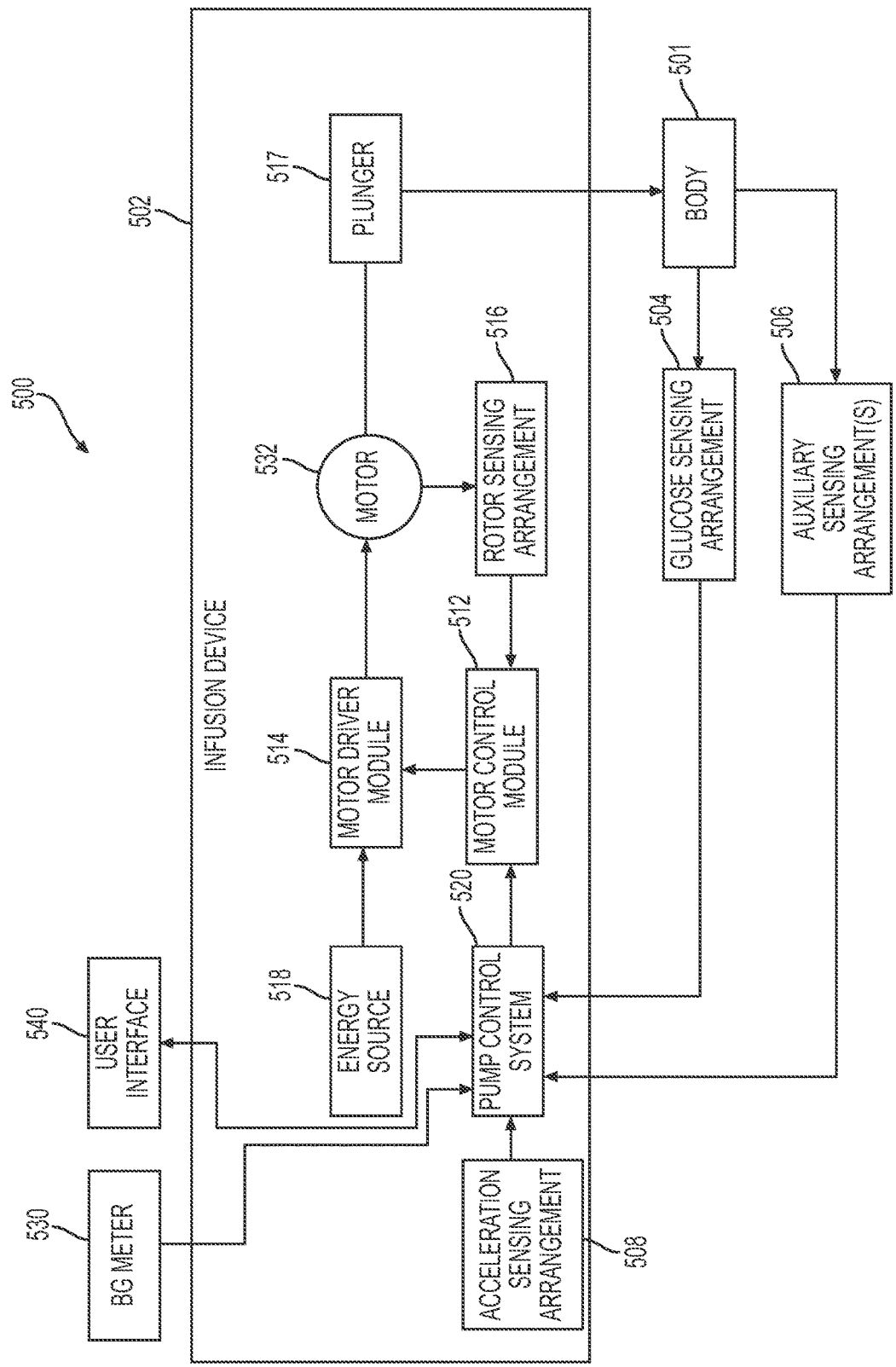
FIG. 5 is a block diagram of an exemplary infusion system suitable for use with a fluid infusion device in one or more embodiments.

FIG. 5 depicts an exemplary embodiment of an infusion system 500 suitable for use with an infusion device 502, such as any one of the infusion devices 102, 200 described above. The infusion system 500 is capable of controlling or otherwise regulating a physiological condition in the body 501 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., a blood glucose sensing arrangement 504) communicatively coupled to the infusion device 502. However, it should be noted that in alternative embodiments, the condition being regulated by the infusion system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the patient's glucose level, which is being regulated in the body 501 of the patient by the infusion system 500.

In exemplary embodiments, the sensing arrangement 504 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 501 of the patient. The output electrical signals are filtered or otherwise processed to obtain a measurement value indicative of the patient's interstitial fluid glucose level. For example, in one implementation, a sensor of the continuous glucose monitor (CGM) measures glucose indirectly via interstitial fluid using, e.g., a subcutaneous sensor. Interstitial fluid is the fluid that surrounds the cells of the patient's tissue below their skin, and usually glucose moves from their blood vessels and capillaries first and then into their interstitial fluid. Thus, sensor glucose readings are taken by the sensing arrangement 504 from the patient's interstitial fluid, and not from their blood, like finger stick measurements. For purposes of explanation, the calibrated blood glucose values that are calculated based on the electrical signals output by the sensing element(s) of the sensing arrangement 504 may alternatively be referred to herein as the sensor glucose (SG) value, the sensed glucose value, or variants thereof. There is a physiological lag between measurements of interstitial SG values versus blood glucose values. As such, in most cases the sensing arrangement 504 needs to be calibrated using a blood glucose meter 530. To explain further, the blood glucose meter 530 measures blood glucose values directly from a blood stream. As such, blood glucose values can refer to glucose values measured directly from a supply of a patient's blood. In this regard, the terms "blood glucose measurement," "measured blood glucose," "blood glucose concentration," "measured blood glucose concentration," and the like may refer to a glucose level, a blood glucose level, a blood glucose concentration, or the like, that has been obtained via any type of glucose sensor. In exemplary embodiments, a blood glucose meter 530, such as a finger stick device, is utilized to directly sense, detect, measure or otherwise quantify the blood glucose in the body 501 of the patient. In this regard, the blood glucose meter 530 outputs or otherwise provides a measured blood glucose value that may be utilized as a reference measurement for calibrating the sensing arrangement 504 and converting a measurement value indicative of the patient's interstitial fluid glucose level into a corresponding calibrated blood glucose value.

In exemplary embodiments, the infusion system 500 also includes one or more additional sensing arrangements 506, 508 configured to sense, detect, measure or otherwise quantify a characteristic of the body 501 of the patient that is indicative of a condition in the body 501 of the patient. In this regard, in addition to the glucose sensing arrangement 504, one or more auxiliary sensing arrangements 506 (also referred to herein as a source of activity data or "activity tracker") may be worn, carried, or otherwise associated with the body 501 of the patient to measure characteristics or conditions of the patient (or the patient's activity) that may influence the patient's glucose levels or insulin sensitivity. For example, a heart rate sensing arrangement 506 could be worn on or otherwise associated with the patient's body 501 to sense, detect, measure or otherwise quantify the patient's heart rate, which, in turn, may be indicative of exercise (and the intensity thereof) that is likely to influence the patient's glucose levels or insulin response in the body 501. In yet another embodiment, another invasive, interstitial, or subcutaneous sensing arrangement 506 may be inserted into the body 501 of the patient to obtain measurements of another physiological condition that may be indicative of exercise (and the intensity thereof), such as, for example, a lactate sensor, a ketone sensor, or the like. Depending on the embodiment, the auxiliary sensing arrangement(s) 506 could be realized as a standalone component worn by the patient, or alternatively, the auxiliary sensing arrangement(s) 506 may be integrated with the infusion device 502 or the glucose sensing arrangement 504.

The illustrated infusion system 500 also includes an acceleration sensing arrangement 508 (or accelerometer) that may be worn on or otherwise associated with the patient's body 501 to sense, detect, measure or otherwise quantify an acceleration of the patient's body 501, which, in turn, may be indicative of exercise or some other condition in the body 501 that is likely to influence the patient's insulin response. While the acceleration sensing arrangement 508 is depicted as being integrated into the infusion device 502 in FIG. 5, in alternative embodiments, the acceleration sensing arrangement 508 may be integrated with another sensing arrangement 504, 506 on the body 501 of the patient, or the acceleration sensing arrangement 508 may be realized as a separate standalone component that is worn by the patient.

In the illustrated embodiment, the pump control system 520 generally represents the electronics and other components of the infusion device 502 that control operation of the fluid infusion device 502 according to a desired infusion delivery program in a manner that is influenced by the sensed glucose value indicating the current glucose level in the body 501 of the patient. For example, to support a closed-loop operating mode, the pump control system 520 maintains, receives, or otherwise obtains a target or commanded glucose value, and automatically generates or otherwise determines dosage commands for operating an actuation arrangement, such as a motor 532, to displace the plunger 517 and deliver insulin to the body 501 of the patient based on the difference between the sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit(s), insulin delivery limit(s), and/or other glucose threshold value(s) in a data storage element accessible to the pump control system 520. As described in greater detail, in one or more exemplary embodiments, the pump control system 520 automatically adjusts or adapts one or more parameters or other control information used to generate commands for operating the motor 532 in a manner that accounts for a likely change in the patient's glucose level or insulin response resulting from a meal, exercise, or other activity.

Still referring to FIG. 5, the target glucose value and other threshold glucose values utilized by the pump control system 520 may be received from an external component (e.g., CCD 106 and/or computing device 108) or be input by a patient via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the patient to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 532 (e.g., motor assembly 207) that is operable to displace a plunger 517 (e.g., plunger 217) in a reservoir (e.g., reservoir 205) and provide a desired amount of fluid to the body 501 of a patient. In this regard, displacement of the plunger 517 results in the delivery of a fluid, such as insulin, that is capable of influencing the patient's physiological condition to the body 501 of the patient via a fluid delivery path (e.g., via tubing 221 of an infusion set 225). A motor driver module 514 is coupled between an energy source 518 and the motor 532. The motor control module 512 is coupled to the motor driver module 514, and the motor control module 512 generates or otherwise provides command signals that operate the motor driver module 514 to provide current (or power) from the energy source 518 to the motor 532 to displace the plunger 517 in response to receiving, from a pump control system 520, a dosage command indicative of the desired amount of fluid to be delivered.

In exemplary embodiments, the energy source 518 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 518 into alternating electrical signals applied to respective phases of the stator windings of the motor 532 that result in current flowing through the stator windings that generates a stator magnetic field and causes the rotor of the motor 532 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 532 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 532 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 532 to achieve the desired delivery of fluid to the patient.

When the motor control module 512 is operating the motor driver module 514, current flows from the energy source 518 through the stator windings of the motor 532 to produce a stator magnetic field that interacts with the rotor magnetic field. In some embodiments, after the motor control module 512 operates the motor driver module 514 and/or motor 532 to achieve the commanded dosage, the motor control module 512 ceases operating the motor driver module 514 and/or motor 532 until a subsequent dosage command is received. In this regard, the motor driver module 514 and the motor 532 enter an idle state during which the motor driver module 514 effectively disconnects or isolates the stator windings of the motor 532 from the energy source 518. In other words, current does not flow from the energy source 518 through the stator windings of the motor 532 when the motor 532 is idle, and thus, the motor 532 does not consume power from the energy source 518 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 502, while in alternative embodiments, the pump control system 520 may be implemented by a remote computing device that is physically distinct and/or separate from the infusion device 502, such as, for example, the CCD 106 or the computing device 108.

Figure 6:
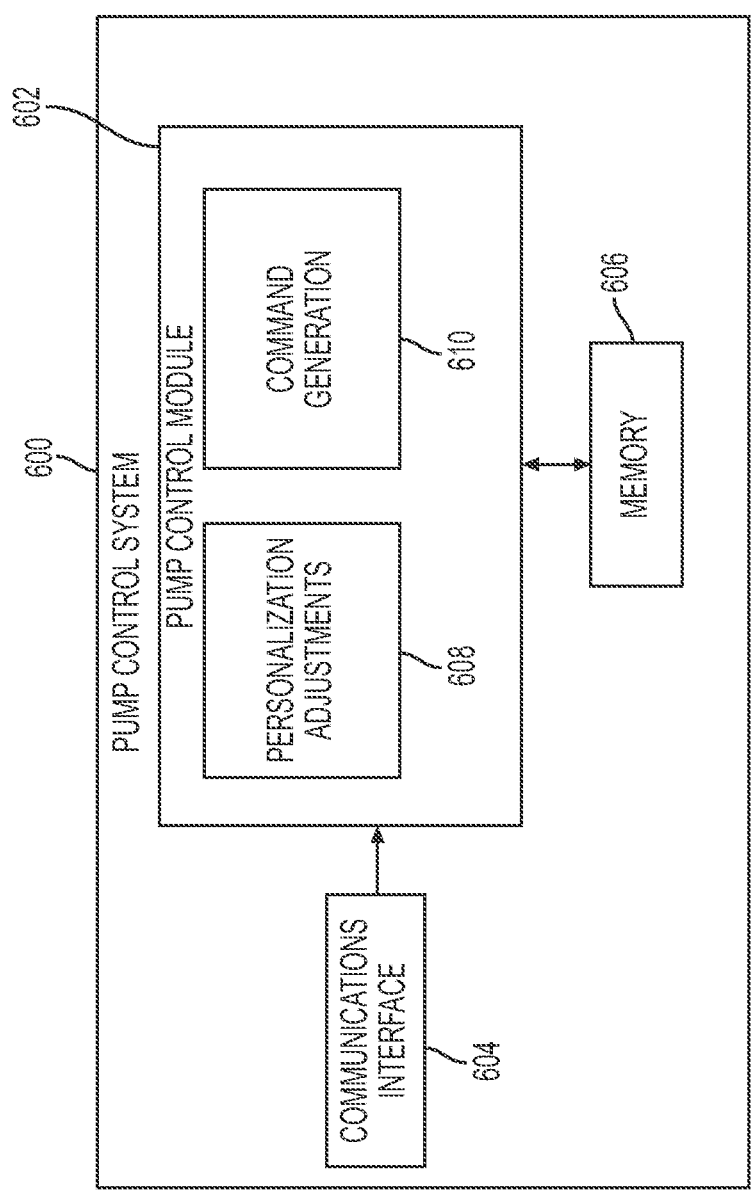
FIG. 6 is a block diagram of an exemplary pump control system suitable for use in the infusion device in the infusion system of FIG. 5 in one or more embodiments.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In various embodiments, the pump control module 602 is also coupled to one or more user interface elements (e.g., user interface 230, 540) for receiving user inputs (e.g., target glucose values or other glucose thresholds) and providing notifications, alerts, or other therapy information to the patient.

The communications interface 604 generally represents the hardware, circuitry, logic, firmware and/or other components of the pump control system 600 that are coupled to the pump control module 602 and configured to support communications between the pump control system 600 and the various sensing arrangements 504, 506, 508. In this regard, the communications interface 604 may include or otherwise be coupled to one or more transceiver modules capable of supporting wireless communications between the pump control system 520, 600 and the sensing arrangement 504, 506, 508. For example, the communications interface 604 may be utilized to receive sensor measurement values or other measurement data from each sensing arrangement 504, 506, 508 in an infusion system 500. In other embodiments, the communications interface 604 may be configured to support wired communications to/from the sensing arrangement(s) 504, 506, 508. In various embodiments, the communications interface 604 may also support communications with another electronic device (e.g., CCD 106 and/or computer 108) in an infusion system (e.g., to upload sensor measurement values to a server or other computing device, receive control information from a server or other computing device, and the like).

The pump control module 602 generally represents the hardware, circuitry, logic, firmware and/or other component of the pump control system 600 that is coupled to the communications interface 604 and configured to determine dosage commands for operating the motor 532 to deliver fluid to the body 501 based on measurement data received from the sensing arrangements 504, 506, 508 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 532 of the infusion device 502 in an autonomous operating mode based at least in part on a current measurement value for a condition in the body 501 of the patient. For example, in a closed-loop operating mode, the command generation application 610 may determine a dosage command for operating the motor 532 to deliver insulin to the body 501 of the patient based at least in part on the current glucose measurement value most recently received from the sensing arrangement 504 to regulate the patient's blood glucose level to a target reference glucose value. Additionally, the command generation application 610 may generate dosage commands for boluses that are manually-initiated or otherwise instructed by a patient via a user interface element.

In exemplary embodiments, the pump control module 602 also implements or otherwise executes a personalization application 608 that is cooperatively configured to interact with the command generation application 610 to support adjusting dosage commands or control information dictating the manner in which dosage commands are generated in a personalized, patient-specific manner. In this regard, in some embodiments, based on correlations between current or recent measurement data and the current operational context relative to historical data associated with the patient, the personalization application 608 may adjust or otherwise modify values for one or more parameters utilized by the command generation application 610 when determining dosage commands, for example, by modifying a parameter value at a register or location in memory 606 referenced by the command generation application 610. In yet other embodiments, the personalization application 608 may predict meals or other events or activities that are likely to be engaged in by the patient and output or otherwise provide an indication of the predicted patient behavior for confirmation or modification by the patient, which, in turn, may then be utilized to adjust the manner in which dosage commands are generated to regulate glucose in a manner that accounts for the patient's behavior in a personalized manner.

Still referring to FIG. 6, depending on the embodiment, the pump control module 602 may be implemented or realized with at least one general purpose processor device, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the applications 608, 610 and perform tasks, operations, functions, and processes described herein.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case the separate motor control module 512 may be absent from an embodiment of the infusion device 502.

Figure 7:
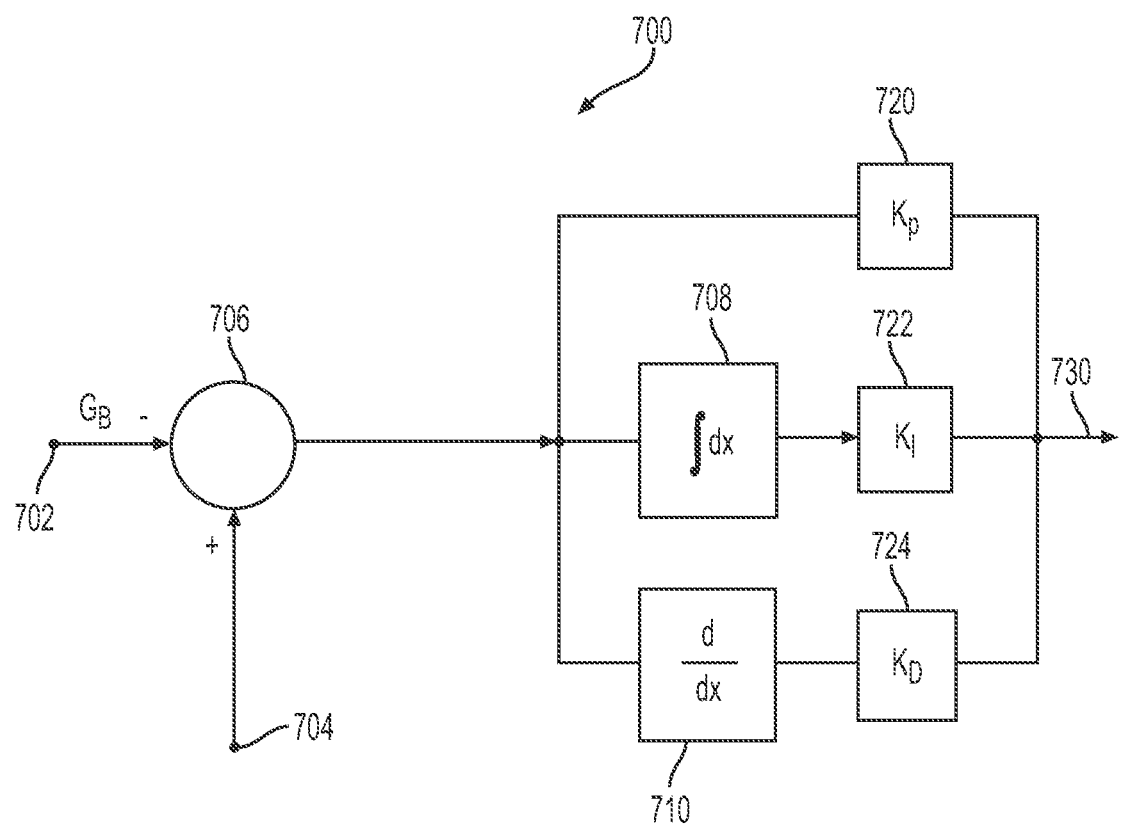
FIG. 7 is a block diagram of a closed-loop control system that may be implemented or otherwise supported by the pump control system in the fluid infusion device of FIGS. 5-6 in one or more exemplary embodiments.

FIG. 7 depicts an exemplary closed-loop control system 700 that may be implemented by a pump control system 520, 600 to provide a closed-loop operating mode that autonomously regulates a condition in the body of a patient to a reference (or target) value. In this regard, the control system 700 can be utilized to regulate the delivery of insulin to the patient during an automatic basal insulin delivery operation. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value (e.g., the most recently obtained sensor glucose value) from the sensing arrangement 504 at input 704. The illustrated control system 700 implements or otherwise provides proportional-integral-derivative (PID) control to determine or otherwise generate delivery commands for operating the motor 532 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 532 to deliver insulin to the body of the patient to influence the patient's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, $K_P$, to obtain the proportional term. The integral term path includes an integration block 708 that integrates the difference and a gain block 722 that multiplies the integrated difference by an integral gain coefficient, $K_I$, to obtain the integral term. The derivative term path includes a derivative block 710 that determines the derivative of the difference and a gain block 724 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 730. Various implementation details pertaining to closed-loop PID control and determining gain coefficients are described in greater detail in U.S. Pat. No. 7,402,153, which is incorporated by reference.

In one or more exemplary embodiments, the PID gain coefficients are patient-specific and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

In one or more exemplary embodiments, one or more parameters of the closed-loop control system 700 are automatically adjusted or adapted in a personalized manner to account for potential changes in the patient's glucose level or insulin sensitivity resulting from meals, exercise, or other events or activities. For example, in one or more embodiments, the target glucose value may be decreased in advance of a predicted meal event to achieve an increase in the insulin infusion rate to effectively pre-bolus a meal, and thereby reduce the likelihood of postprandial hyperglycemia. Additionally, or alternatively, the time constant or gain coefficient associated with one or more paths of the closed-loop control system 700 may be adjusted to tune the responsiveness to deviations between the measured glucose value and the target glucose value. For example, based on the particular type of meal being consumed or the particular time of day during which the meal is consumed, the time constant associated with the derivative block 710 or derivative term path may be adjusted to make the closed-loop control more or less aggressive in response to an increase in the patient's glucose level based on the patient's historical glycemic response to the particular type of meal.

Figure 8:
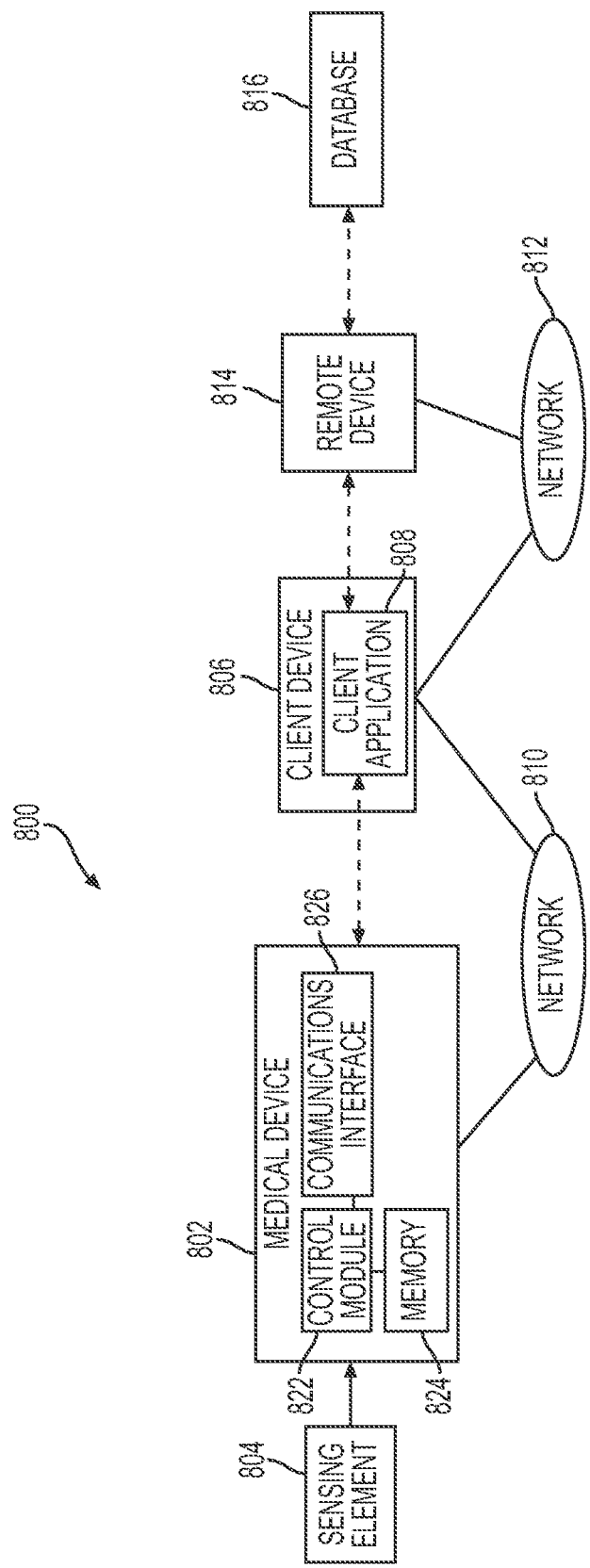
FIG. 8 is a block diagram of an exemplary patient monitoring system.

FIG. 8 depicts an exemplary embodiment of a patient monitoring system 800. The patient monitoring system 800 includes a medical device 802 that is communicatively coupled to a sensing element 804 that is inserted into the body of a patient or otherwise worn by the patient to obtain measurement data indicative of a physiological condition in the body of the patient, such as a sensed glucose level. The medical device 802 is communicatively coupled to a client device 806 via a communications network 810, with the client device 806 being communicatively coupled to a remote device 814 via another communications network 812. In this regard, the client device 806 may function as an intermediary for uploading or otherwise providing measurement data from the medical device 802 to the remote device 814. It should be appreciated that FIG. 8 depicts a simplified representation of a patient monitoring system 800 for purposes of explanation and is not intended to limit the subject matter described herein in any way.

In exemplary embodiments, the client device 806 is realized as a mobile phone, a smartphone, a tablet computer, or other similar mobile electronic device; however, in other embodiments, the client device 806 may be realized as any sort of electronic device capable of communicating with the medical device 802 via network 810, such as a laptop or notebook computer, a desktop computer, or the like. In exemplary embodiments, the network 810 is realized as a Bluetooth network, a ZigBee network, or another suitable personal area network. That said, in other embodiments, the network 810 could be realized as a wireless ad hoc network, a wireless local area network (WLAN), or local area network (LAN). The client device 806 includes or is coupled to a display device, such as a monitor, screen, or another conventional electronic display, capable of graphically presenting data and/or information pertaining to the physiological condition of the patient. The client device 806 also includes or is otherwise associated with a user input device, such as a keyboard, a mouse, a touchscreen, or the like, capable of receiving input data and/or other information from the user of the client device 806.

In exemplary embodiments, a user, such as the patient, the patient's doctor or another healthcare provider, or the like, manipulates the client device 806 to execute a client application 808 that supports communicating with the medical device 802 via the network 810. In this regard, the client application 808 supports establishing a communications session with the medical device 802 on the network 810 and receiving data and/or information from the medical device 802 via the communications session. The medical device 802 may similarly execute or otherwise implement a corresponding application or process that supports establishing the communications session with the client application 808. The client application 808 generally represents a software module or another feature that is generated or otherwise implemented by the client device 806 to support the processes described herein. Accordingly, the client device 806 generally includes a processing system and a data storage element (or memory) capable of storing programming instructions for execution by the processing system, that, when read and executed, cause processing system to create, generate, or otherwise facilitate the client application 808 and perform or otherwise support the processes, tasks, operations, and/or functions described herein. Depending on the embodiment, the processing system may be implemented using any suitable processing system and/or device, such as, for example, one or more processor devices, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof In one or more embodiments, the client device 806 and the medical device 802 establish an association (or pairing) with one another over the network 810 to support subsequently establishing a point-to-point or peer-to-peer communications session between the medical device 802 and the client device 806 via the network 810. For example, in accordance with one embodiment, the network 810 is realized as a Bluetooth network, wherein the medical device 802 and the client device 806 are paired with one another (e.g., by obtaining and storing network identification information for one another) by performing a discovery procedure or another suitable pairing procedure. The pairing information obtained during the discovery procedure allows either of the medical device 802 or the client device 806 to initiate the establishment of a secure communications session via the network 810.

In one or more exemplary embodiments, the client application 808 is also configured to store or otherwise maintain an address and/or other identification information for the remote device 814 on the second network 812. In this regard, the second network 812 may be physically and/or logically distinct from the network 810, such as, for example, the Internet, a cellular network, a wide area network (WAN), or the like. The remote device 814 generally represents a server or other computing device configured to receive and analyze or otherwise monitor measurement data, event log data, and potentially other information obtained for the patient associated with the medical device 802. In exemplary embodiments, the remote device 814 is coupled to a database 816 configured to store or otherwise maintain data associated with individual patients. In practice, the remote device 814 may reside at a location that is physically distinct and/or separate from the medical device 802 and the client device 806, such as, for example, at a facility that is owned and/or operated by or otherwise affiliated with a manufacturer of the medical device 802. For purposes of explanation, but without limitation, the remote device 814 may alternatively be referred to herein as a server.

Still referring to FIG. 8, the sensing element 804 generally represents the component of the patient monitoring system 800 that is configured to generate, produce, or otherwise output one or more electrical signals indicative of a physiological condition that is sensed, measured, or otherwise quantified by the sensing element 804. In this regard, the physiological condition of a patient influences a characteristic of the electrical signal output by the sensing element 804, such that the characteristic of the output signal corresponds to or is otherwise correlative to the physiological condition that the sensing element 804 is sensitive to. In exemplary embodiments, the sensing element 804 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 804.

The medical device 802 generally represents the component of the patient monitoring system 800 that is communicatively coupled to the output of the sensing element 804 to receive or otherwise obtain the measurement data samples from the sensing element 804 (e.g., the measured glucose and characteristic impedance values), store or otherwise maintain the measurement data samples, and upload or otherwise transmit the measurement data to the remote device 814 or server via the client device 806. In one or more embodiments, the medical device 802 is realized as an infusion device 102, 200, 502 configured to deliver a fluid, such as insulin, to the body of the patient. That said, in other embodiments, the medical device 802 could be a standalone sensing or monitoring device separate and independent from an infusion device (e.g., sensing arrangement 104, 504). It should be noted that although FIG. 8 depicts the medical device 802 and the sensing element 804 as separate components, in practice, the medical device 802 and the sensing element 804 may be integrated or otherwise combined to provide a unitary device that can be worn by the patient.

In exemplary embodiments, the medical device 802 includes a control module 822, a data storage element 824 (or memory), and a communications interface 826. The control module 822 generally represents the hardware, circuitry, logic, firmware and/or other component(s) of the medical device 802 that is coupled to the sensing element 804 to receive the electrical signals output by the sensing element 804 and perform or otherwise support various additional tasks, operations, functions and/or processes described herein. Depending on the embodiment, the control module 822 may be implemented or realized with a general purpose processor device, a microprocessor device, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 822 includes an analog-to-digital converter (ADC) or another similar sampling arrangement that samples or otherwise converts an output electrical signal received from the sensing element 804 into corresponding digital measurement data value. In other embodiments, the sensing element 804 may incorporate an ADC and output a digital measurement value.

The communications interface 826 generally represents the hardware, circuitry, logic, firmware and/or other components of the medical device 802 that are coupled to the control module 822 for outputting data and/or information from/to the medical device 802 to/from the client device 806. For example, the communications interface 826 may include or otherwise be coupled to one or more transceiver modules capable of supporting wireless communications between the medical device 802 and the client device 806. In exemplary embodiments, the communications interface 826 is realized as a Bluetooth transceiver or adapter configured to support Bluetooth Low Energy (BLE) communications.

In exemplary embodiments, the remote device 814 receives, from the client device 806, measurement data values associated with a particular patient (e.g., sensor glucose measurements, acceleration measurements, and the like) that were obtained using the sensing element 804, and the remote device 814 stores or otherwise maintains the historical measurement data in the database 816 in association with the patient (e.g., using one or more unique patient identifiers). Additionally, the remote device 814 may also receive, from or via the client device 806, meal data or other event log data that may be input or otherwise provided by the patient (e.g., via client application 808) and store or otherwise maintain historical meal data and other historical event or activity data associated with the patient in the database 816. In this regard, the meal data include, for example, a time or timestamp associated with a particular meal event, a meal type or other information indicative of the content or nutritional characteristics of the meal, and an indication of the size associated with the meal. In exemplary embodiments, the remote device 814 also receives historical fluid delivery data corresponding to basal or bolus dosages of fluid delivered to the patient by an infusion device 102, 200, 502. For example, the client application 808 may communicate with an infusion device 102, 200, 502 to obtain insulin delivery dosage amounts and corresponding timestamps from the infusion device 102, 200, 502, and then upload the insulin delivery data to the remote device 814 for storage in association with the particular patient. The remote device 814 may also receive geolocation data and potentially other contextual data associated with a device 802, 806 from the client device 806 and/or client application 808, and store or otherwise maintain the historical operational context data in association with the particular patient. In this regard, one or more of the devices 802, 806 may include a global positioning system (GPS) receiver or similar modules, components or circuitry capable of outputting or otherwise providing data characterizing the geographic location of the respective device 802, 806 in real-time.

The historical patient data may be analyzed by one or more of the remote device 814, the client device 806, and/or the medical device 802 to alter or adjust operation of an infusion device 102, 200, 502 to influence fluid delivery in a personalized manner. For example, the patient's historical meal data and corresponding measurement data or other contextual data may be analyzed to predict a future time when the next meal is likely to be consumed by the patient, the likelihood of a future meal event within a specific time period, the likely size or amount of carbohydrates associated with a future meal, the likely type or nutritional content of the future meal, and/or the like. Moreover, the patient's historical measurement data for postprandial periods following historical meal events may be analyzed to model or otherwise characterize the patient's glycemic response to the predicted size and type of meal for the current context (e.g., time of day, day of week, geolocation, etc.). One or more aspects of the infusion device 102, 200, 502 that control or regulate insulin delivery may then be modified or adjusted to proactively account for the patient's likely meal activity and glycemic response.

In one or more exemplary embodiments, the remote device 814 utilizes machine learning to determine which combination of historical sensor glucose measurement data, historical delivery data, historical auxiliary measurement data (e.g., historical acceleration measurement data, historical heart rate measurement data, and/or the like), historical event log data, historical geolocation data, and other historical or contextual data are correlated to or predictive of the occurrence of a particular event, activity, or metric for a particular patient, and then determines a corresponding equation, function, or model for calculating the value of the parameter of interest based on that set of input variables. Thus, the model is capable of characterizing or mapping a particular combination of one or more of the current (or recent) sensor glucose measurement data, auxiliary measurement data, delivery data, geographic location, patient behavior or activities, and the like to a value representative of the current probability or likelihood of a particular event or activity or a current value for a parameter of interest. It should be noted that since each patient's physiological response may vary from the rest of the population, the subset of input variables that are predictive of or correlative for a particular patient may vary from other patients. Additionally, the relative weightings applied to the respective variables of that predictive subset may also vary from other patients who may have common predictive subsets, based on differing correlations between a particular input variable and the historical data for that particular patient. It should be noted that any number of different machine learning techniques may be utilized by the remote device 814 to determine what input variables are predictive for a current patient of interest, such as, for example, artificial neural networks, genetic programming, support vector machines, Bayesian networks, probabilistic machine learning models, or other Bayesian techniques, fuzzy logic, heuristically derived combinations, or the like.

The insulin infusion device may incorporate or leverage the control algorithms, processing schemes, and operating methodologies (or suitably modified, updated, or customized versions thereof) of the type described in U.S. Pat. No. 9,526,834 and International (PCT) patent publication number WO 2014/035570; the content of these published documents is incorporated herein by reference.

Figure 9:
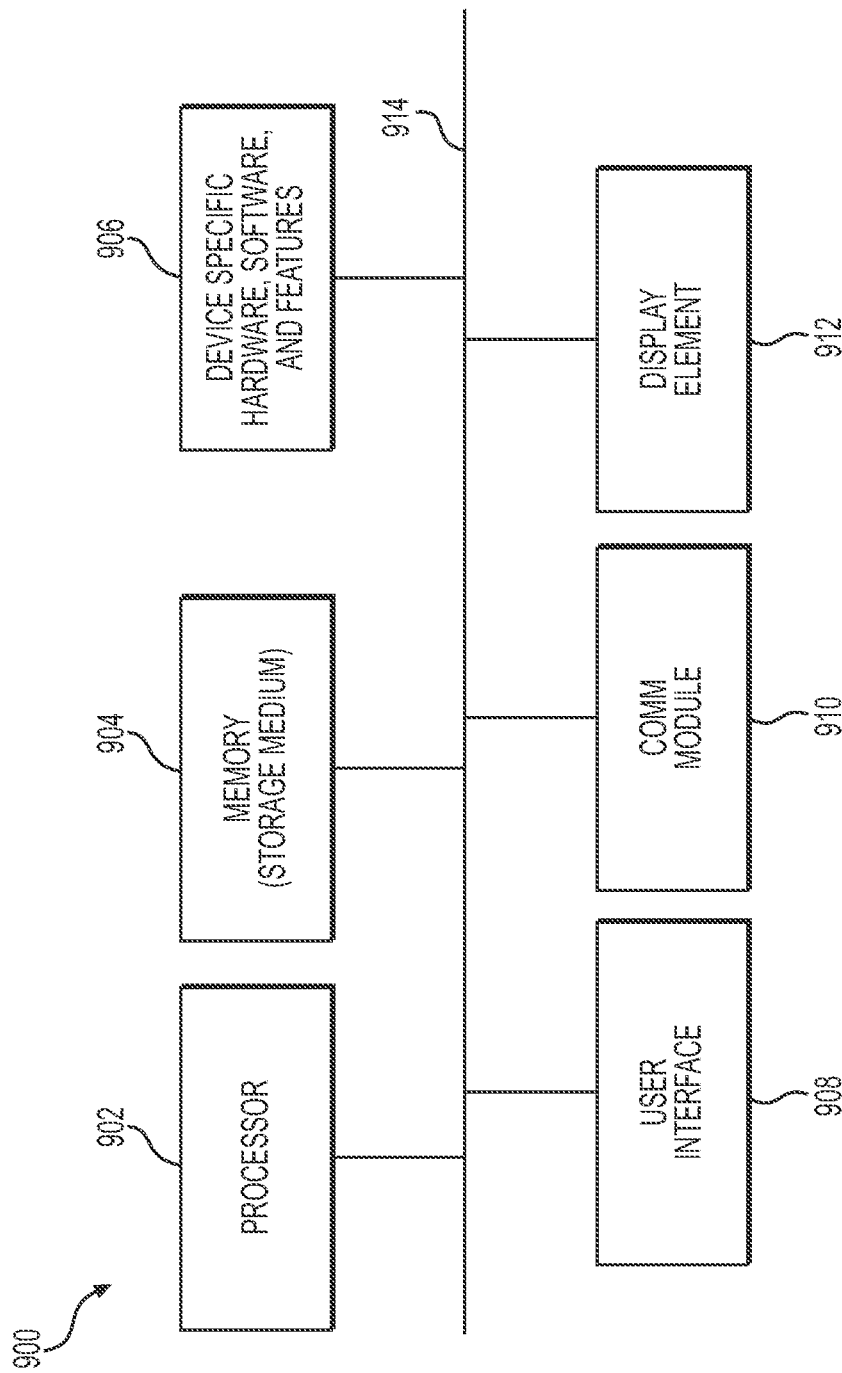
FIG. 9 is a simplified block diagram representation of an exemplary embodiment of a computer-based or processor-based device suitable for deployment in the system shown in FIG. 1.

Each of the devices or components that are described above with reference to FIGS. 1-8 can be realized as a computer-based or processor-based component. As such, an exemplary embodiment of a computer-based or processor-based device 900 will be described with reference to FIG. 9, which is a simplified block diagram representation of an exemplary embodiment of the computer-based or processor-based device 900 that is suitable for deployment in the systems shown in FIGS. 1-8. In addition, the computer-based or processor-based device 900 that will be described with reference to FIG. 9 can also be used to implement a system 1000 that includes an estimation model 1040 for estimating glucose values, as will be described below with reference to FIGS. 10-12.

The illustrated embodiment of the device 900 is intended to be a high-level and generic representation of one suitable platform. In this regard, any of the computer-based or processor-based components of the system 100 can utilize the architecture of the device 900. The illustrated embodiment of the device 900 generally includes, without limitation: at least one processor 902; a suitable amount of memory 904; device-specific hardware, software, firmware, and/or features 906; a user interface 908; a communication module 910; and a display element 912. Of course, an implementation of the device 900 may include additional elements, components, modules, and functionality configured to support various features that are unrelated to the subject matter described here. For example, the device 900 may include certain features and elements to support conventional functions that might be related to the particular implementation and deployment of the device 900. In practice, the elements of the device 900 may be coupled together via a bus or any suitable interconnection architecture 914.

The processor 902 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. Moreover, the processor 902 may be implemented as a combination of computing devices, e.g., a combination of a digital signal processor and a microprocessor, a plurality of microprocessors, one or more microprocessors in conjunction with a digital signal processor core, or any other such configuration.

The memory 904 may be realized as RAM memory, flash memory, EPROM memory, EEPROM memory, registers, a hard disk, a removable disk, a CD-ROM, or any other form of storage medium known in the art. In this regard, the memory 904 can be coupled to the processor 902 such that the processor 902 can read information from, and write information to, the memory 904. In the alternative, the memory 904 may be integral to the processor 902. As an example, the processor 902 and the memory 904 may reside in an ASIC. At least a portion of the memory 904 can be realized as a computer storage medium, e.g., a tangible computer-readable medium having computer-executable instructions stored thereon. The computer-executable instructions, when read and executed by the processor 902, cause the device 900 to perform certain tasks, operations, functions, and processes that are specific to the particular embodiment. In this regard, the memory 904 may represent one suitable implementation of such computer-readable media. Alternatively, or additionally, the device 900 could receive and cooperate with computer-readable media (not separately shown) that is realized as a portable or mobile component or platform, e.g., a portable hard drive, a USB flash drive, an optical disc, or the like.

The device-specific hardware, software, firmware, and features 906 may vary from one embodiment of the device 900 to another. For example, the device-specific hardware, software, firmware, and features 906 will support: smartphone functions and features when the device 900 is realized as a mobile telephone; conventional personal computer functions and features if the device 900 is realized as a laptop or tablet computer; insulin pump operations when the device 900 is realized as an insulin infusion device; etc. In practice, certain portions or aspects of the device-specific hardware, software, firmware, and features 906 may be implemented in one or more of the other blocks depicted in FIG. 9.

The user interface 908 may include or cooperate with various features to allow a user to interact with the device 900. Accordingly, the user interface 908 may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 900. The user interface 908 may include one or more graphical user interface (GUI) control elements that enable a user to manipulate or otherwise interact with an application via the display element 912.

The communication module 910 facilitates data communication between the device 900 and other components as needed during the operation of the device 900. In the context of this description, the communication module 910 can be employed to transmit or stream device-related control data, patient-related data, device-related status or operational data, glycemic insight messages and notifications, and the like. It should be appreciated that the particular configuration and functionality of the communication module 910 can vary depending on the hardware platform and specific implementation of the device 900. In practice, an embodiment of the device 900 may support wireless data communication and/or wired data communication, using various data communication protocols. For example, the communication module 910 could support one or more wireless data communication protocols, techniques, or methodologies, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication module 910 could support one or more wired/cabled data communication protocols, including, without limitation: Ethernet; powerline; home network communication protocols; USB; IEEE 1394 (Firewire); hospital network communication protocols; and proprietary data communication protocols.

The display element 912 is suitably configured to enable the device 900 to render and display various screens, insight messages, notifications, GUIs, GUI control elements, drop down menus, auto-fill fields, text entry fields, message fields, or the like. Of course, the display element 912 may also be utilized for the display of other information during the operation of the device 900, as is well understood. Notably, the specific configuration, operating characteristics, size, resolution, and functionality of the display element 910 can vary depending upon the practical implementation of the device 900. For example, if the device 900 is a laptop computer, then the display element 912 may be a relatively large monitor. Alternatively, if the device 900 is a cellular telephone device, then the display element 912 may be a relatively small integrated display screen, such as a touch-sensitive screen.

Figure 10:
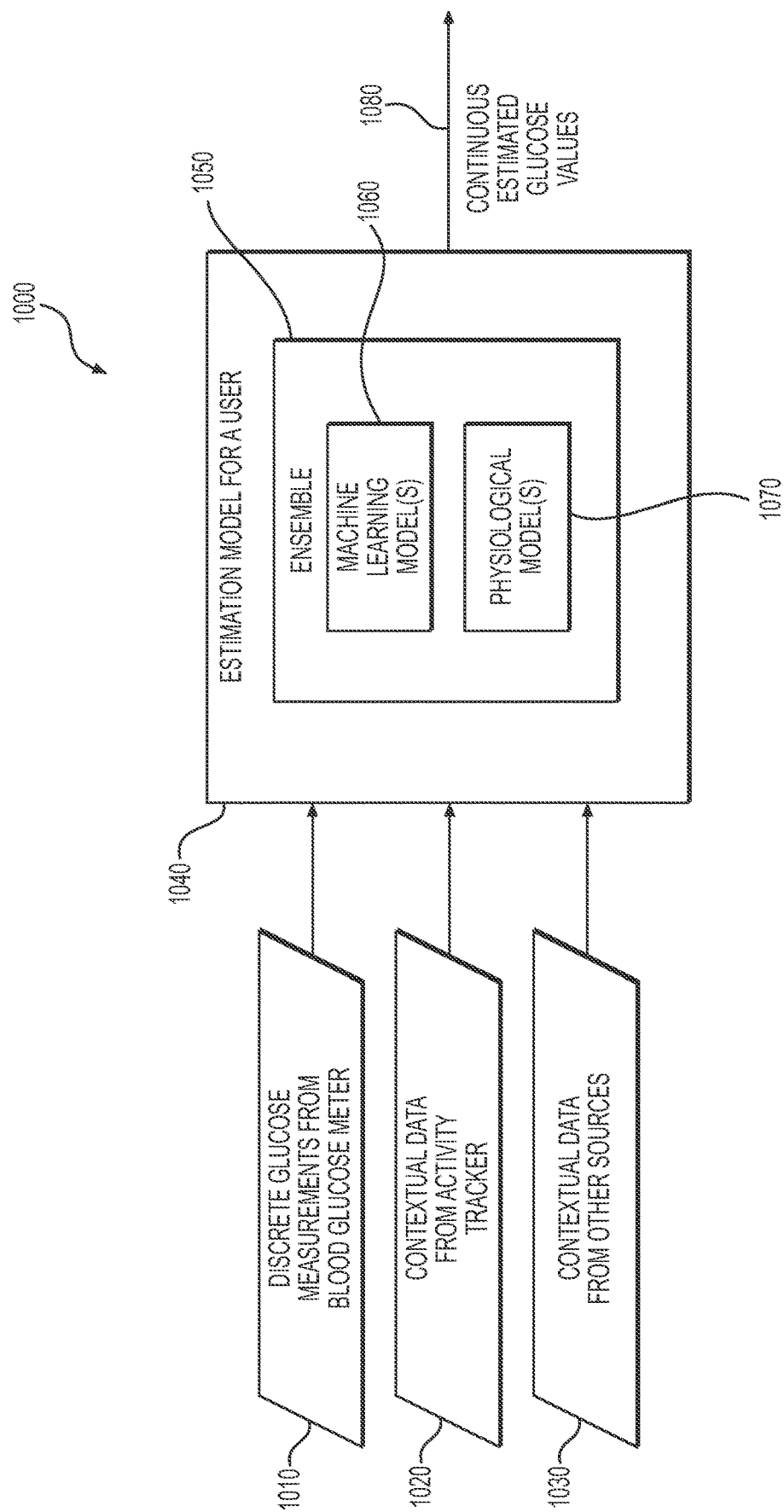
FIG. 10 is a block diagram of a system for estimating glucose values for a particular user or patient in accordance of the disclosed embodiments.

FIG. 10 is a block diagram of a system 1000 for estimating glucose values for a particular user or patient in accordance of the disclosed embodiments. The system 1000 includes an estimation model 1040 that is configured to receive various inputs 1010, 1020, 1030. The estimation model 1040 can be executed at a processing system. The processing system can be implemented at any of the devices described herein including those illustrated and described above with reference to FIGS. 1 and 8, and more generically at a computer-based or processor-based device 900 such as that illustrated and described above with reference to FIG. 9. For instance, the processing system can be implemented at a backend server system, such as, the remote device 814 of FIG. 8, at a client device 806 of FIG. 8 (e.g., patient's smartphone), at a medical device 802 of FIG. 8 (e.g., an insulin infusion device 502 of FIG. 5) or other end device, such as the auxiliary sensing arrangement(s) 506 (or activity tracker device, ring, necklace, vest, etc.) and the blood glucose meter 530 of FIG. 5. Thus, in one embodiment, the processing system can be implemented at a backend server system, such as, the remote device 814 of FIG. 8. For example, the estimation model can be executed or run as part of a web application at the backend server system, and the backend server system can then communicate the estimated glucose values to a client device (e.g., patient's smartphone), an insulin infusion device or other end device. In another embodiment, the processing system can be implemented at a client device and the estimation model can be executed as part of a mobile application at the client device. In another embodiment, the processing system can be implemented at an insulin infusion device and the estimation model can be executed as part of an application at the insulin infusion device.

In one nonlimiting embodiment, the inputs include discrete glucose measurements 1010 from a blood glucose meter (BGM), contextual activity data 1020 from an activity tracker or equivalent source of activity data such as a smartphone or other health related device, and optionally contextual data 1030 from other sources. The contextual activity data 1020 collected from the activity tracker or equivalent source of activity data (e.g., smartphone or other health related device) can include, for example, one or more of: metabolic data about the patient (e.g., calories burned); physical activity data about the user (e.g., heart rate data for the patient, exercise data for the patient, activity type, duration and intensity data, data about a number of steps taken by the patient during a time period, metabolic equivalents and other parameters); data from a fitness or exercise advisor device or application that provides fitness/exercise suggestions or recommendations to users; and other raw contextual data such as accelerometer (x,y,z) data, geolocation data, iBeacon location data, skin temperature data, ambient air temperature data, bioimpedance heart rate data, sweat data (e.g., GSR-conductance), blood pressure data, shake detection data, pedometer data, barometer data, gyroscope data, meal log data, orientation (azimuth, pitch, roll (degrees)) data; health kit data (such as data from Apple® Healthkit, Google® Fit, etc.), medication/prescription information data, user gestures data, uv light detector data, magnetometer data, respiration data, muscle activity data, pulse oximeter data, blood+interstitial fluid pH data, METS data, sleep quality/time data, EMR and lab data, etc. The contextual data 1030 from other sources can include, for example, historical sensor glucose measurement data, historical delivery data, historical auxiliary measurement data such as historical acceleration measurement data, historical heart rate measurement data, skin conductance, and/or the like, historical event log data, historical geolocation data, and other historical or contextual data are correlated to or predictive of the occurrence of a particular event, activity, or metric for a particular patient. The estimation model 1040 processes at least some of the various inputs to continuously generate estimated glucose values 1080.

In one or more exemplary embodiments, the remote device 814 of FIG. 8 utilizes machine learning to determine, based on discrete glucose measurements 1010 from a blood glucose meter (e.g. the blood glucose meter 530 of FIG. 5), contextual activity data 1020 from as the auxiliary sensing arrangement(s) 506 (e.g., from "activity tracker" or equivalent source of activity data), and optionally contextual data 1030 from other sources, to generate continuous estimated glucose values 1080. Depending on the implementation, the machine learning model 1060 can be a corresponding equation, function, or model for calculating the estimated glucose values 1080 based on the set of input variables. Thus, the machine learning model 1060 is capable of characterizing or mapping a particular combination of inputs to a value representative of the estimated glucose values 1080.

Artificial intelligence is an area of computer science emphasizes the creation of intelligent machines that work and react like humans. Some of the activities computers with artificial intelligence are designed for include learning. Examples of artificial intelligence algorithms include, but are not limited to, key learning, actor critic methods, reinforce, deep deterministic policy gradient (DDPG), multi-agent deep deterministic policy gradient (MADDPG), etc. Machine learning refers to an artificial intelligence discipline geared toward the technological development of human knowledge.

Machine learning facilitates a continuous advancement of computing through exposure to new scenarios, testing and adaptation, while employing pattern and trend detection for improved decisions and subsequent, though not identical, situations. Machine learning (ML) algorithms and statistical models can be used by computer systems to effectively perform a specific task without using explicit instructions, relying on patterns and inference instead. Machine learning algorithms build a mathematical model based on sample data, known as "training data," in order to make predictions or decisions without being explicitly programmed to perform the task. Machine learning algorithms can be used when it is infeasible to develop an algorithm of specific instructions for performing the task.

For example, supervised learning algorithms build a mathematical model of a set of data that contains both the inputs and the desired outputs. The data is known as training data and consists of a set of training examples. Each training example has one or more inputs and a desired output, also known as a supervisory signal. In the case of semi-supervised learning algorithms, some of the training examples are missing the desired output. In the mathematical model, each training example is represented by an array or vector, and the training data by a matrix. Through iterative optimization of an objective function, supervised learning algorithms learn a function that can be used to predict the output associated with new inputs. An optimal function will allow the algorithm to correctly determine the output for inputs that were not a part of the training data. An algorithm that improves the accuracy of its outputs or predictions over time is said to have learned to perform that task. Supervised learning algorithms include classification and regression. Classification algorithms are used when the outputs are restricted to a limited set of values, and regression algorithms are used when the outputs may have any numerical value within a range. Similarity learning is an area of supervised machine learning closely related to regression and classification, but the goal is to learn from examples using a similarity function that measures how similar or related two objects are.

Reinforcement learning is an area of machine learning concerned with how software agents ought to take actions in an environment so as to maximize some notion of cumulative reward. Due to its generality, the field is studied in many other disciplines, such as game theory, control theory, operations research, information theory, simulation-based optimization, multi-agent systems, swarm intelligence, statistics and genetic algorithms. In machine learning, the environment is typically represented as a Markov Decision Process (MDP). Many reinforcement learning algorithms use dynamic programming techniques. Reinforcement learning algorithms do not assume knowledge of an exact mathematical model of the MDP and are used when exact models are infeasible.

In accordance with one non-limiting implementation, the estimation model 1040 can be an ensemble model 1050. An ensemble model 1050 includes two or more related, but different analytical models that are run or executed at the same time, where the results generated by each can then be synthesized into a single score or spread in order to improve the accuracy of predictive analytics. To explain further, in predictive modeling and other types of data analytics, a single model based on one data sample can have biases, high variability or outright inaccuracies that can affect the reliability of its analytical findings. By combining different models or analyzing multiple samples, the effects of those limitations can be reduced to provide better information. As such, ensemble methods can use multiple machine learning algorithms to obtain better predictive performance than could be obtained from any of the constituent learning algorithms alone.

An ensemble is a supervised learning algorithm because it can be trained and then used to make predictions. The trained ensemble, therefore, represents a single hypothesis that is not necessarily contained within the hypothesis space of the models from which it is built. Thus, ensembles can be shown to have more flexibility in the functions they can represent. An ensemble model can include a set of individually trained classifiers (such as neural networks or decision trees) whose predictions are combined.

For instance, one common example of ensemble modeling is a random forest model which is a type of analytical model that leverages multiple decision trees and is designed to predict outcomes based on different variables and rules. A random forest model blends decision trees that may analyze different sample data, evaluate different factors or weight common variables differently. The results of the various decision trees are then either converted into a simple average or aggregated through further weighting. The emergence of Hadoop and other big data technologies has allowed greater volumes of data to be stored and analyzed, which can allow analytical models to be run on different data samples.

In one embodiment, the ensemble model 1050 can include or be built using at least one machine learning model 1060 and a physiological model 1070. The physiological model 1070 can be, for example, a population-based model of one or more equations (e.g., a set of differential equations) that are generally applicable to any patient, but has different variables or parameters that are weighted in accordance with a particular patient's individual parameters to mimic the physiology of that patient. In other words, because each patient's physiological response may vary from the rest of the population, the relative weightings applied to the respective variables of the physiological model 1070 may also vary from other patients. The physiological model 1070 can be used in conjunction with the machine learning model(s) 1060 to help confine estimations or predictions within a realistic range.

Depending on the implementation, any number of machine learning models can be combined to optimize the ensemble model 1050. Examples of machine learning algorithms or models that can be implemented at the machine learning model 1060 can include, but are not limited to: regression models such as linear regression, logistic regression, and K-means clustering; one or more decision tree models (e.g., a random forest model); one or more support vector machines; one or more artificial neural networks; one or more deep learning networks (e.g., at least one recurrent neural network, sequence to sequence mapping using deep learning, sequence encoding using deep learning, etc.); fuzzy logic based models; genetic programming models; Bayesian networks or other Bayesian techniques, probabilistic machine learning models; Gaussian processing models; Hidden Markov models; time series methods such as Autoregressive Moving Average (ARMA) models, Autoregressive Integrated Moving Average (ARIMA) models, Autoregressive conditional heteroskedasticity (ARCH) models; generalized autoregressive conditional heteroskedasticity (GARCH) models; moving-average (MA) models or other models; and heuristically derived combinations of any of the above, etc. The types of machine learning algorithms differ in their approach, the type of data they input and output, and the type of task or problem that they are intended to solve.

A Hidden Markov model (HMM) is a statistical Markov model in which the system being modeled is assumed to be a Markov process with unobserved (hidden) states. An MINI can be considered as the simplest dynamic Bayesian network. A Bayesian network, belief network or directed acyclic graphical model is a probabilistic graphical model that represents a set of random variables and their conditional independence with a directed acyclic graph (DAG). Bayesian networks that model sequences of variables are called dynamic Bayesian networks. Generalizations of Bayesian networks that can represent and solve decision problems under uncertainty are called influence diagrams.

Support vector machines (SVMs), also known as support vector networks, are a set of related supervised learning methods used for classification and regression. Given a set of training examples, each marked as belonging to one of two categories, an SVM training algorithm builds a model that predicts whether a new example falls into one category or the other. An SVM training algorithm is a non-probabilistic, binary, linear classifier. In addition to performing linear classification, SVMs can efficiently perform a non-linear classification using what is called the kernel trick, implicitly mapping their inputs into high-dimensional feature spaces.

Decision tree learning uses a decision tree as a predictive model to go from observations about an item (represented in the branches) to conclusions about the item's target value (represented in the leaves). Tree models where the target variable can take a discrete set of values are called classification trees; in these tree structures, leaves represent class labels and branches represent conjunctions of features that lead to those class labels. Decision trees where the target variable can take continuous values (typically real numbers) are called regression trees. In decision analysis, a decision tree can be used to visually and explicitly represent decisions and decision making.

Deep learning algorithms can refer to a collection of algorithms used in machine learning, that are used to model high-level abstractions and data through the use of model architectures, which are composed of multiple nonlinear transformations. Deep learning is a specific approach used for building and training neural networks. Deep learning consists of multiple hidden layers in an artificial neural network. Examples of deep learning algorithms can include, for example, Siamese networks, transfer learning, recurrent neural networks (RNNs), long short term memory (LSTM) networks, convolutional neural networks (CNNs), transformers, etc. For instance, deep learning approaches can make use of autoregressive Recurrent Neural Networks (RNN), such as the long short-term memory (LSTM) and the Gated Recurrent Unit (GRU). One neural network architecture for time series forecasting using RNNs (and variants) is an autoregressive seq2seq neural network architecture, which acts as an autoencoder.

In some embodiments, the ensemble model 1050 can include one or more deep learning algorithms. It should be noted that any number of different machine learning techniques may also be utilized. Depending on the implementation, the ensemble model 1050 can be implemented as a bootstrap aggregating ensemble algorithm (also referred to as a bagging classifier method), as a boosting ensemble algorithm or classifier algorithm, as a stacking ensemble algorithm or classifier algorithm, as bucket of models ensemble algorithms, as Bayes optimal classifier algorithms, as Bayesian parameter averaging algorithms, as Bayesian model combination algorithms, etc.

Bootstrap aggregating, often abbreviated as bagging, involves having each model in the ensemble vote with equal weight. In order to promote model variance, bagging trains each model in the ensemble using a randomly drawn subset of the training set. As an example, the random forest algorithm combines random decision trees with bagging to achieve very high classification accuracy. A bagging classifier or ensemble method creates individuals for its ensemble by training each classifier on a random redistribution of the training set. Each classifier's training set can be generated by randomly drawing, with replacement, N examples—where N is the size of the original training set; many of the original examples may be repeated in the resulting training set while others may be left out. Each individual classifier in the ensemble is generated with a different random sampling of the training set. Bagging is effective on "unstable" learning algorithms (e.g., neural networks and decision trees), where small changes in the training set result in large changes in predictions.

By contrast, boosting involves incrementally building an ensemble by training each new model instance to emphasize the training instances that previous models mis-classified. In some cases, boosting has been shown to yield better accuracy than bagging, but it also tends to be more likely to over-fit the training data. A boosting classifier can refer to a family of methods that can be used to produce a series of classifiers. The training set used for each member of the series is chosen based on the performance of the earlier classifier(s) in the series. In boosting, examples that are incorrectly predicted by previous classifiers in the series are chosen more often than examples that were correctly predicted. Thus, boosting attempts to produce new classifiers that are better able to predict examples for which the current ensemble's performance is poor. A common implementation of boosting is Adaboost, although some newer algorithms are reported to achieve better results.

Stacking (sometimes called stacked generalization) involves training a learning algorithm to combine the predictions of several other learning algorithms. Stacking works in two phases: multiple base classifiers are used to predict the class, and then a new learner is used to combine their predictions with the aim of reducing the generalization error. First, all of the other algorithms are trained using the available data, then a combiner algorithm is trained to make a final prediction using all the predictions of the other algorithms as additional inputs. If an arbitrary combiner algorithm is used, then stacking can theoretically represent any of the ensemble techniques described in this article, although, in practice, a logistic regression model is often used as the combiner.

A "bucket of models" is an ensemble technique in which a model selection algorithm is used to choose the best model for each problem. When tested with only one problem, a bucket of models can produce no better results than the best model in the set, but when evaluated across many problems, it will typically produce much better results, on average, than any model in the set. One common approach used for model-selection is cross-validation selection (sometimes called a "bake-off contest"). Cross-validation selection can be summed up as try them all with the training set and pick the one that works best. Gating is a generalization of Cross-Validation Selection. It involves training another learning model to decide which of the models in the bucket is best-suited to solve the problem. Often, a perceptron is used for the gating model. It can be used to pick the "best" model, or it can be used to give a linear weight to the predictions from each model in the bucket. When a bucket of models is used with a large set of problems, it may be desirable to avoid training some of the models that take a long time to train. Landmark learning is a meta-learning approach that seeks to solve this problem. It involves training only the fast (but imprecise) algorithms in the bucket, and then using the performance of these algorithms to help determine which slow (but accurate) algorithm is most likely to do best.

The Bayes optimal classifier is a classification technique. It is an ensemble of all the hypotheses in the hypothesis space. On average, no other ensemble can outperform it. The naive Bayes optimal classifier is a version of this that assumes that the data is conditionally independent on the class and makes the computation more feasible. Each hypothesis is given a vote proportional to the likelihood that the training dataset would be sampled from a system if that hypothesis were true. To facilitate training data of finite size, the vote of each hypothesis is also multiplied by the prior probability of that hypothesis. The hypothesis represented by the Bayes optimal classifier, however, is the optimal hypothesis in ensemble space (the space of all possible ensembles.

Bayesian parameter averaging (BPA) is an ensemble technique that seeks to approximate the Bayes optimal classifier by sampling hypotheses from the hypothesis space and combining them using Bayes' law. Unlike the Bayes optimal classifier, Bayesian model averaging (BMA) can be practically implemented. Hypotheses are typically sampled using a Monte Carlo sampling technique such as MCMC. For example, Gibbs sampling may be used to draw hypotheses that are representative of a distribution. It has been shown that under certain circumstances, when hypotheses are drawn in this manner and averaged according to Bayes' law, this technique has an expected error that is bounded to be at most twice the expected error of the Bayes optimal classifier.

Bayesian model combination (BMC) is an algorithmic correction to Bayesian model averaging (BMA). Instead of sampling each model in the ensemble individually, it samples from the space of possible ensembles (with model weightings drawn randomly from a Dirichlet distribution having uniform parameters). This modification overcomes the tendency of BMA to converge toward giving all of the weight to a single model. Although BMC is somewhat more computationally expensive than BMA, it tends to yield dramatically better results. The results from BMC have been shown to be better on average (with statistical significance) than BMA, and bagging. The use of Bayes' law to compute model weights necessitates computing the probability of the data given each model. Typically, none of the models in the ensemble are exactly the distribution from which the training data were generated, so all of them correctly receive a value close to zero for this term. This would work well if the ensemble were big enough to sample the entire model-space, but such is rarely possible. Consequently, each pattern in the training data will cause the ensemble weight to shift toward the model in the ensemble that is closest to the distribution of the training data. It essentially reduces to an unnecessarily complex method for doing model selection. The possible weightings for an ensemble can be visualized as lying on a simplex. At each vertex of the simplex, all of the weight is given to a single model in the ensemble. BMA converges toward the vertex that is closest to the distribution of the training data. By contrast, BMC converges toward the point where this distribution projects onto the simplex. In other words, instead of selecting the one model that is closest to the generating distribution, it seeks the combination of models that is closest to the generating distribution. The results from BMA can often be approximated by using cross-validation to select the best model from a bucket of models. Likewise, the results from BMC may be approximated by using cross-validation to select the best ensemble combination from a random sampling of possible weightings.

Figure 11:
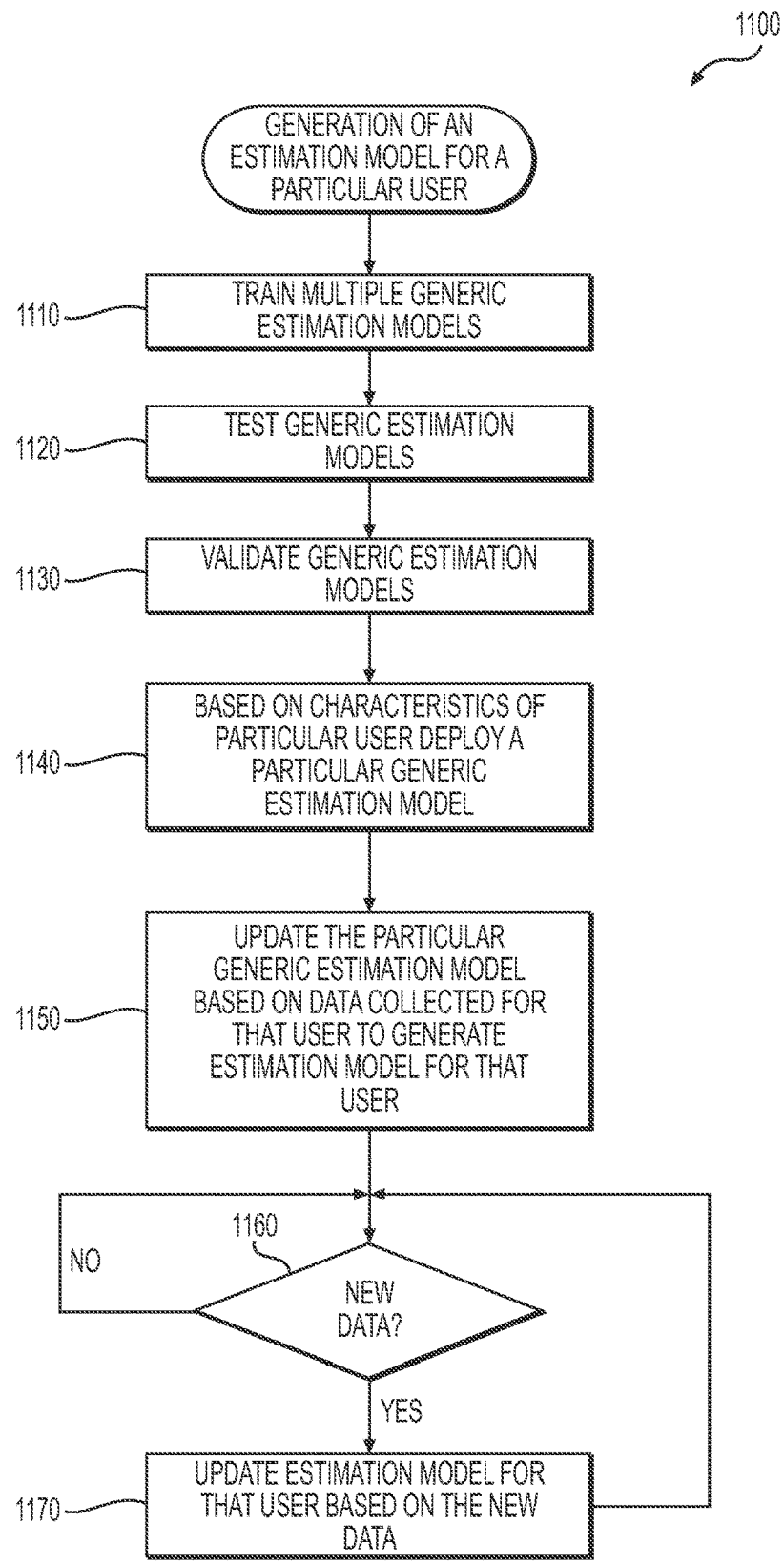
FIG. 11 is a flowchart that illustrates a method for generating an estimation model for a particular patient in accordance with the disclosed embodiments.

FIG. 11 is a flowchart that illustrates a method 1100 for generating an estimation model for a particular patient in accordance with the disclosed embodiments. The method 1100 begins at 1110 where a computing system trains multiple generic estimation models. Each generic estimation model can be modeled for a particular group of users. At 1120, the computing system tests the generic estimation models, and then at 1130, the computing system validates the generic estimation models. For example, in one embodiment, the computing system can train multiple population-base models for type 1 and type 2 patients using different combinations of demographic parameters such as age, gender, location and diabetes history such as diabetes onset, years on insulin, therapy type using existing BG, insulin, meal information, activity data from an activity tracker, and CGM data to train, test and validate the models.

Once all the generic estimation models have been validated, the method 1100 proceeds to 1140, where the computing system determines, based on characteristics of a particular user or patient, an applicable generic estimation model that is the best fit for that particular patient based on characteristics of that particular patient. The particular generic estimation model that is applicable for a particular patient varies based on the characteristics of that particular patient.

At 1150, the computing system can then update the particular generic estimation model that was deployed at 1140 based on data that was collected for that particular patient to generate an estimation model for that particular patient. In other words, parameters of the generic estimation model that was selected and deployed 1140 can be updated and fine-tuned at 150 based on data that was collected for the particular patient in order to customize that generic estimation model such that it becomes an estimation model for that particular patient.

After the estimation model for that particular patient has been generated at 1150 it can be executed and updated any time new data is received for that patient. For example, in one embodiment, the new data can come from the blood glucose meter data (e.g., new blood glucose measurements), new contextual activity data that is received for that patient from the activity tracker, and/or new contextual data that is received for that patient from other sources. In one implementation, the estimation model for that particular patient can be updated each time there is a new data from the BGM. In another embodiment, the new data can be from a continuous glucose monitor. For instance, the CGM can be used periodically to collect CGM data for the particular patient for a certain period of time (e.g., for two weeks), and this newly collected CGM data can then be used to assess performance of the estimation model and/or update or re-train the estimation model for that particular patient. In addition, the CGM data can also be used to train and update the generic estimation models that were described above with reference to step 1110. Furthermore, in some implementations, the CGM data can also be used at 1140 to select and deploy a different one of the generic estimation models for the particular patient.

As such, at 1160, the computing system regularly determines whether new data is received, and if so, the method proceeds to 1170 where the estimation model for that particular patient is updated based on the new data to generate an updated estimation model that can be executed at a processing system (as will be described below).

After the estimation model for that particular patient is updated based on the new data at 1170, the method loops to 1160. As the estimation model for the particular patient is updated it becomes more fine-tuned and can be used to generate better estimated glucose values for the patient. In any point the estimation model can be used to estimate glucose values for the patient. One non-limiting embodiment will now be described with respect to FIG. 12 where an estimation model is used to estimate glucose values for a patient.

Figure 12:
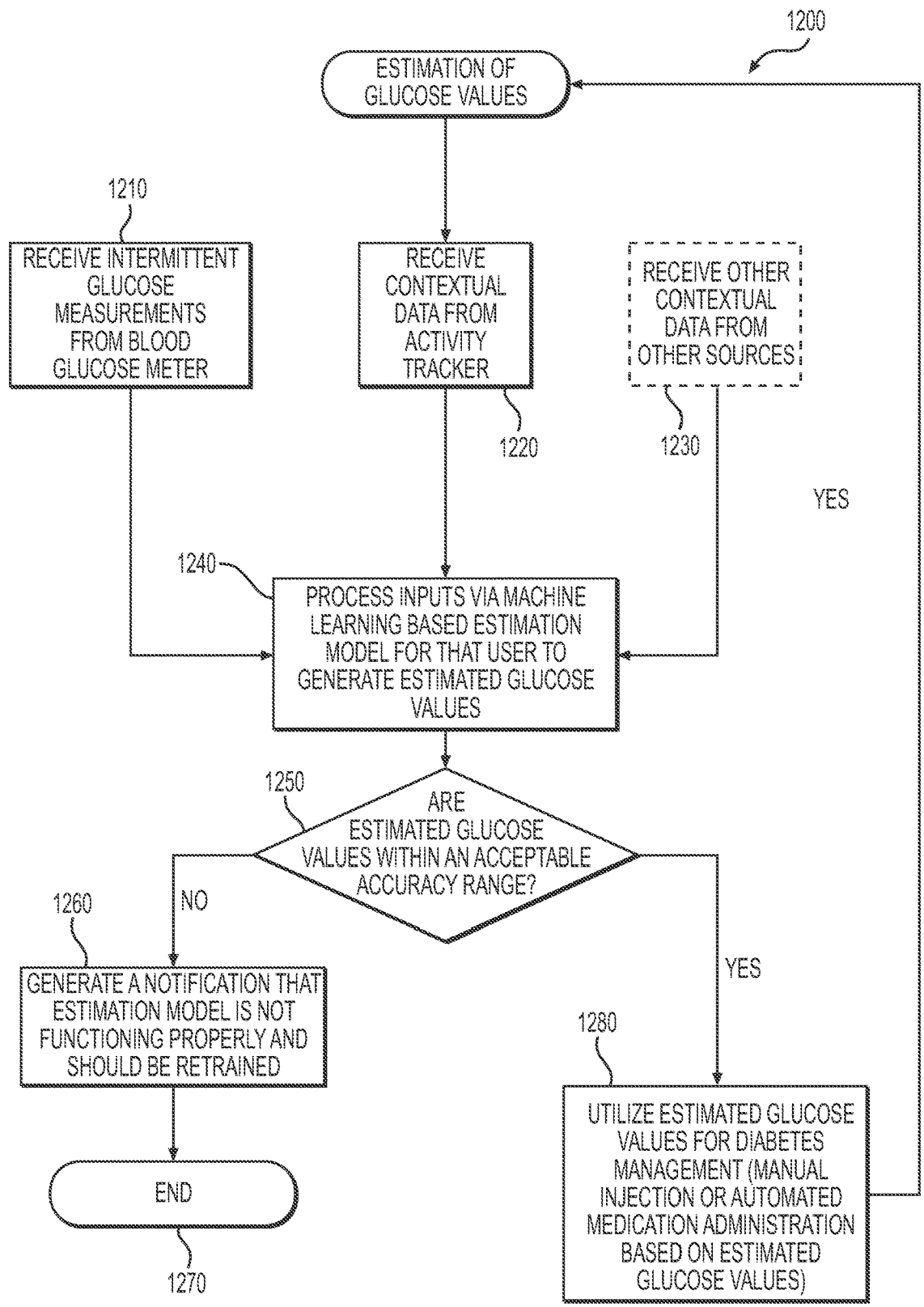
FIG. 12 is a flowchart of a method in accordance of the disclosed embodiments.

FIG. 12 is a flowchart of a method 1200 in accordance of the disclosed embodiments. At 1210, a processing system can receive intermittent glucose measurements from a blood glucose meter. At 1220 the processing system can also receive contextual activity data from an activity tracker. At 1230, the processing system can also optionally receive other contextual data from other sources that are described above. In one embodiment, a first set of inputs comprising a sequence of intermittent blood glucose measurements are received from the calibrated blood glucose meter, and a second set of user inputs comprising contextual activity data collected from the user by an activity tracker are received from the activity tracker. Optionally, the other contextual data from other sources can include, for example, a third set of inputs from an insulin infusion device comprising insulin dispensed by the insulin infusion device and/or a fourth set of inputs comprising user entries that describe meal information.

At 1240, a processing system can execute the machine learning-based estimation model for that patient to process the various inputs from steps 1210, 1220, 1230 to generate a sequence or set of estimated glucose values for that particular patient. The estimated glucose values are analogous to glucose measurements that can be taken by a glucose sensor in that the estimated glucose values estimate continuous glucose sensor measurement values. However, the processing system can generate the set of estimated glucose values without using information from a continuous glucose sensor arrangement. This can eliminate the need for a continuous glucose sensor, which can be a relatively expensive component with respect to a blood glucose meter, and thus saves patients a significant cost. It may also support intermittent CGM users that take "sensor vacations" due to various reasons which may include access, discomfort, seasonal needs, etc. In one embodiment, only the first set of inputs and the second set of user inputs are processed via the estimation model to generate the set of estimated glucose values. As used herein, "estimated glucose value," and "estimated glucose concentration," and the like may refer to a glucose level that has been estimated via the machine learning-based estimation model. In one embodiment, the estimated glucose values estimate and track interstitial or sensor glucose values (e.g., that are generated by a sensing arrangement such as a CGM device that has been calibrated using measured blood glucose values measured by a blood glucose meter).

Steps 1250-1280 are optional and relate to when and how the estimated glucose values can be used within the context of an insulin management system for diabetes management. For example, in one implementation, at 1250, the computing system can monitor the set or sequence of estimated glucose values (e.g., discrete estimates of blood glucose levels) to determine if the sequence of the estimated glucose values are within an acceptable accuracy range that allows them to be used by an insulin management system. How the computing system can determine if the sequence of the estimated glucose values are within an acceptable accuracy range can vary depending on the implementation. For example, in one embodiment, the computing system can determine if the sequence of the estimated glucose values are within an acceptable accuracy range by measuring a difference between estimated glucose value and intermittent glucose measurements from a blood glucose meter (or equivalent device) and then comparing that difference to an accuracy threshold. In another embodiment, the computing system can determine if the sequence of the estimated glucose values are within an acceptable accuracy range by measuring difference between estimated glucose value and periodic measurements that were taken by a CGM device and then comparing that difference to an accuracy threshold.

When the estimated glucose values are determined (at 1250) to not be within an acceptable accuracy range that allows them to be used by an insulin management system, the method 1200 proceeds to 1260, where a notification or an alert can be generated that can be perceptible to the patient or another user who is monitoring the patient. For example, in one embodiment, when the estimated glucose values are not in acceptable accuracy ranges, a notification or alert can be generated to inform the user that they should not trust the estimated glucose values being generated by the estimation model and to recommend that the user to wear another sensor (e.g., CGM) to retrain the estimation model. Any number of alerting methodologies can be employed at step 1260, including, but not limited to, presenting (via a display device) graphical elements and text associated with notifications and alerts for the glucose control system (see reference 100, FIG. 1). In one embodiment, notifications and alerts can be presented by an insulin pump device associated with a computing device and/or presented via a communicatively coupled personal computing device (e.g., a laptop computer, a tablet computer, a smartphone). Such notifications and alerts may include, without limitation: audio alerts (e.g., sound effects, articulated speech alerts, alarms), visual alerts (e.g., graphical elements and text presented via user interface or display of the insulin delivery pump, text effects, flashing or otherwise activated lights, color changes), text alerts (e.g., a text-based message transmitted via Short Message Service (SMS), an email message transmitted via the internet), and/or any other type of alert generated to attract the attention of the user. In addition, in some embodiments, when it is determined (at 1250) that the estimated glucose values are not within an acceptable accuracy range (that allows them to be used by an insulin management system), one or more displays may be controlled so that the estimated glucose values are not presented to the user. Following 1260, the method 1200 can then end at 1270.

When the estimated glucose values are determined (at 1250) to be within an acceptable accuracy range that allows them to be used by an insulin management system, the method 1200 proceeds to 1280, where the estimated glucose values can be utilized the insulin delivery system, and estimates can continue to be generated in near real-time. The actions that can be taken at the insulin delivery system based on the estimated glucose values vary depending on the implementation. For example, actions that can be taken at the insulin delivery system based on the estimated glucose values can include controlling an insulin infusion device based on the estimated glucose values so that it administers insulin to a patient, or generating a notification or an alert, based on the estimated glucose values, that can be perceptible to the patient or another user who is monitoring the patient. As will be described below, the corrective actions and the notifications or alerts that can be generated vary depending on the implementation.

For example, in one implementation of step 1280, the computing system operates cooperatively with an insulin delivery system and the machine learning-based estimation model to monitor estimated glucose levels of a patient, and to identify abnormalities in the estimated glucose levels. For example, the computing system can monitor the set or sequence of estimated glucose values (e.g., discrete estimates of blood glucose levels) to determine if the sequence of the estimated glucose values are within a low range, a high range, or an acceptable range. For instance, hypoglycemia is a deficiency of glucose in the bloodstream of the patient or user of the insulin delivery pump. Hypoglycemia may be generally associated with glucose values below 70 milligrams per deciliter (mg/dL), depending on certain patient-specific factors. Hyperglycemia is an excess of glucose in the bloodstream of the patient or user of the insulin delivery pump and may be generally associated with glucose values above 180 mg/dL, depending on certain patient-specific factors. Normal, healthy blood glucose levels, over every 24-hour cycle, generally range between 70 and 160 mg/dL. An abnormality in a sequence of blood glucose levels may include blood glucose levels below a predefined hypoglycemia threshold, blood glucose levels above a predefined hyperglycemia threshold, a decreasing blood glucose trend approaching or below a predefined hypoglycemia threshold, an increasing blood glucose trend approaching or above a predefined hyperglycemia threshold, or the like.

The abnormality indicates that a corrective action is required to maintain blood glucose stability at appropriate levels. Abnormalities in blood glucose levels require intervention to bring the patient's blood glucose levels into a safe and healthy range. As such, when the estimated glucose values are not within an acceptable range, the method 1200 can proceed to 1280, where a corrective action can be taken at the insulin infusion device to deliver the patient an amount of insulin required to adequately treat the blood glucose abnormality to bring the blood glucose levels of the patient within normal limits and/or regulate their blood sugar levels. For example, in one embodiment, the estimated glucose values can be used to control and drive an insulin infusion device so that it administers insulin to a patient.

Exemplary embodiments of corrective actions are disclosed in, for example, in U.S. patent application Ser. No. 16/129,552, filed Sep. 12, 2018, entitled "SYSTEMS AND METHODS FOR ALERTING A USER TO DETECTED EFFECTS OF A RECENT THERAPY ADJUSTMENT," and assigned to the assignee of the present invention, which is incorporated herein by reference in its entirety. Any number of corrective actions or intervention methodologies can be employed at step 1280, such as, administration of a bolus of insulin (to decrease blood glucose levels) or administration of a quantity of carbohydrates, glucose, or other medication (to increase blood glucose levels). In other words, the corrective action may include the administration of a bolus of insulin (to decrease hyperglycemic blood glucose levels) or the administration of a dose of carbohydrates (to increase hypoglycemic blood glucose levels).

In addition, in one embodiment, at step 1280, the computing system operates cooperatively with an insulin delivery system (e.g., insulin pump or manual insulin injection device such as an insulin pen) and the machine learning-based estimation model to monitor estimated glucose levels of a patient, and to generate a notification or an alert, based on the estimated glucose values, that can be perceptible to the patient or another user who is monitoring the patient (e.g., to inform the patient or the user of any abnormalities that are detected when the estimated glucose values are within the low range that is too low or within the high range that is too high). For instance, a notification or alert can be sent to the user to alert them that estimated glucose values are abnormal and help drive decision support for medication administration. Exemplary embodiments of alerts are disclosed, for example, in U.S. patent application Ser. No. 16/129,552, filed Sep. 12, 2018, entitled "SYSTEMS AND METHODS FOR ALERTING A USER TO DETECTED EFFECTS OF A RECENT THERAPY ADJUSTMENT," and assigned to the assignee of the present invention, which is incorporated herein by reference in its entirety. Any number of alerting methodologies can be employed at step 1280, including, but not limited to, presenting (via a display device) graphical elements and text associated with notifications and alerts for the glucose control system (see reference 100, FIG. 1). In one embodiment, notifications and alerts can be presented by an insulin pump device associated with a computing device and/or presented via a communicatively coupled personal computing device (e.g., a laptop computer, a tablet computer, a smartphone). Such notifications and alerts may include, without limitation: audio alerts (e.g., sound effects, articulated speech alerts, alarms), visual alerts (e.g., graphical elements and text presented via user interface or display of the insulin delivery pump, text effects, flashing or otherwise activated lights, color changes), text alerts (e.g., a text-based message transmitted via Short Message Service (SMS), an email message transmitted via the internet), and/or any other type of alert generated to attract the attention of the user.

For example, a presentation module can identify appropriate graphical elements for presentation via a display device that identify a current estimated blood glucose level (e.g., various icons, text, and/or graphical elements associated with estimated blood glucose levels of a patient), a detected indication of a change of direction in the sequence of blood glucose levels, timing data associated with a detected indication of a change of direction in the sequence of blood glucose levels, an indication that a corrective action should be taken by a user, confirmation of a user-input indication that a corrective action has been completed by a user, and the like.

For example, a display device can display, render, or otherwise convey one or more graphical representations or images associated with blood glucose levels, an indication of a change of direction in a blood glucose trend, and/or notifications or alerts associated with blood glucose levels on the display device. In one embodiment, an alert can notify the patient of an over-corrected or under-corrected abnormality. For instance, in one implementation, an alert can be presented via the insulin delivery pump or a manual insulin injection device (e.g., insulin pen), such that the patient is informed that an administered corrective action has not affected the blood glucose levels of the patient in the desired manner (e.g., that the corrective action has over-corrected or under-corrected the abnormality).

In one embodiment, an alert can be presented to prompt a user to perform a corrective action, in response to a detected abnormality (e.g., blood glucose levels that are too high or too low). For example, when the abnormality includes blood glucose levels that are too high, the user (patient or health care partner) can be prompted to input a command for the insulin delivery pump to administer a bolus of insulin, via the insulin deliver pump, to treat the high blood glucose levels. Alternatively, a notification can provide health care providers with information to adjust basal rate settings of an inulin infusion device so that they are appropriate for a particular patient to meet their needs. In another embodiment, when the abnormality includes blood glucose levels that are too high, the user (patient or health care partner) can be prompted to input a command at a manual insulin injection device (e.g., insulin pen) to administer insulin. By contrast, when the abnormality includes blood glucose levels that are too low, the alert can prompt the user to administer a dose of carbohydrates to treat the low blood glucose levels.

Additionally, the estimated glucose values can be utilized by other downstream systems, such as a fitness or exercise advisor device or application that provides fitness/exercise suggestions or recommendations to users. For instance, the estimated glucose values can be utilized in conjunction with a predicted exercise level in the short future (using similar exercise pattern from the past few minutes) to tell patient if keeping current level of activity will reduce hyperglycemia or introduce hypoglycemia.

After 1280, the method 1280 can loop to the start, and then proceeds to steps 1210, 1220 and 1230 to wait and receive new data regarding blood glucose measurements from a blood glucose meter, contextual activity data from an activity tracker and/or other contextual data from other sources and the model would be retrained.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A processor-implemented method, comprising:
   receiving a first set of inputs comprising contextual activity data collected from a source of user activity data, and a second set of inputs comprising intermittent glucose measurements provided from a blood glucose meter; and
   processing, via an estimation model, the first set of inputs and the second set of inputs to generate a set of estimated real-time glucose values without using information from a continuous glucose monitor, wherein the generated set of estimated real-time glucose values are not inputted into the estimation model, and the estimation model is an ensemble model that comprises: one or more machine learning models, and a physiological model, wherein the physiological model is configured to be used in conjunction with the one or more machine learning models to confine the generated set of estimated real-time glucose values within an acceptable range.

2. The method of claim 1, wherein the one or more machine learning models comprise at least one of:
   one or more artificial neural networks;
   one or more regression models;
   one or more decision tree models;
   one or more Bayesian networks;
   one or more probabilistic machine learning models;
   one or more Gaussian processing models; or
   one or more Hidden Markov models.

3. The method of claim 1, wherein the contextual activity data collected from the source of user activity data comprises one or more of:
   metabolic data about a user; or
   physical activity data about the user.

4. The method of claim 1, wherein the receiving comprises:
   receiving the first set of inputs comprising the contextual activity data collected from the source of user activity data, the second set of inputs comprising intermittent glucose measurements provided from the blood glucose meter, a third set of inputs comprising nutritional information input by a user, and a fourth set of inputs comprising insulin delivered by an insulin infusion device of the user; and
   wherein the processing comprises:
   processing, via the estimation model, the first set of inputs, the second set of inputs, the third set of inputs and the fourth set of inputs to generate the set of estimated real-time glucose values, wherein the set of estimated real-time glucose values track actual glucose values.

5. The method of claim 1, wherein the processing is performed at a server system, wherein the estimation model is executed as part of a web application at the server system, and wherein the server system is configured to communicate results of generation of the set of estimated real-time glucose values to one or more of a client device and an insulin infusion device.

6. The method of claim 1, wherein the processing is performed at:
   a client device, and wherein the estimation model is executed as part of a mobile application at the client device.

7. The method of claim 1, wherein the processing is performed at:
   an insulin infusion device.

8. The method of claim 1, further comprising:
   generating a notification that responsive to determining that the set of estimated real-time glucose values are not within an acceptable accuracy range; or
   controlling delivery of insulin by an insulin infusion device based on the set of estimated real-time glucose values responsive to determining that the set of estimated real-time glucose values are within the acceptable accuracy range.

9. The method of claim 1, wherein the physiological model comprises a population-based model comprising one or more parameters weighted in accordance with one or more physiological parameters of a user.

10. A computing device comprising:
one or more processors; and
one or more processor-readable media storing instructions which, when executed by the one or more processors, cause performance of one or more operations comprising:
receiving a first set of inputs comprising contextual activity data collected from a source of user activity data, and a second set of inputs comprising intermittent glucose measurements provided from a blood glucose meter; and
processing, via an estimation model, the first set of inputs and the second set of inputs to generate a set of estimated real-time glucose values without using information from a continuous glucose monitor, wherein the generated set of estimated real-time glucose values are not inputted into the estimation model, and the estimation model is an ensemble model that comprises: one or more machine learning models; and a physiological model, wherein the physiological model is configured to be used in conjunction with the one or more machine learning models to confine the generated set of estimated real-time glucose values within an acceptable range.

11. The computing device of claim 10, wherein the one or more machine learning models comprise at least one of:
one or more artificial neural networks;
one or more regression models;
one or more decision tree models;
one or more Bayesian networks;
one or more probabilistic machine learning models;
one or more Gaussian processing models; or
one or more Hidden Markov models.

12. The computing device of claim 10, wherein the contextual activity data collected from the source of user activity data comprises one or more of:
metabolic data about a user; or
physical activity data about the user.

13. The computing device of claim 10, the one or more operations further comprising:
generating a notification responsive to determining that the set of estimated real-time glucose values are not within an acceptable accuracy range; or
controlling delivery of insulin by an insulin infusion device based on the set of estimated real-time glucose values responsive to determining that the set of estimated real-time glucose values are within the acceptable accuracy range.

14. The computing device of claim 10, wherein the receiving comprises:
receiving the first set of inputs comprising the contextual activity data collected from the source of user activity data, the second set of inputs comprising intermittent glucose measurements provided from the blood glucose meter, a third set of inputs comprising nutritional information input by a user, and a fourth set of inputs comprising insulin delivered by an insulin infusion device of the user; and
wherein the processing comprises:
processing, via the estimation model, the first set of inputs, the second set of inputs, the third set of inputs and the fourth set of inputs to generate the set of estimated real-time glucose values, wherein the set of estimated real-time glucose values track actual glucose values.

15. The computing device of claim 10, wherein the physiological model comprises a population-based model comprising one or more parameters weighted in accordance with one or more physiological parameters of a user.

16. One or more non-transitory processor-readable media storing instructions which, when executed by one or more processors, cause performance of:
receiving a first set of inputs comprising contextual activity data collected from a source of user activity data, and a second set of inputs comprising intermittent glucose measurements provided from a blood glucose meter; and
processing, via an estimation model, the first set of inputs and the second set of inputs to generate a set of estimated real-time glucose values without using information from a continuous glucose monitor, wherein the generated set of estimated real-time glucose values are not inputted into the estimation model, and the estimation model is an ensemble model that comprises: one or more machine learning models; and a physiological model, wherein the physiological model is configured to be used in conjunction with the one or more machine learning models to confine the generated set of estimated real-time glucose values within an acceptable range.

17. The one or more non-transitory processor-readable media of claim 16, wherein the one or more machine learning models comprise at least one of:
one or more artificial neural networks;
one or more regression models;
one or more decision tree models;
one or more Bayesian networks; one or more probabilistic machine learning models;
one or more Gaussian processing models; or
one or more Hidden Markov models.

18. The one or more non-transitory processor-readable media of claim 16, wherein the receiving comprises:
receiving the first set of inputs comprising the contextual activity data collected from the source of user activity data, the second set of inputs comprising intermittent glucose measurements provided from the blood glucose meter, a third set of inputs comprising nutritional information input by a user, and a fourth set of inputs comprising insulin delivered by an insulin infusion device of the user; and
wherein the processing comprises:
processing, via the estimation model, the first set of inputs, the second set of inputs, the third set of inputs and the fourth set of inputs to generate the set of estimated real-time glucose values.

19. The one or more non-transitory processor-readable media of claim 16, further storing instructions which, when executed by the one or more processors, cause performance of:
generating a notification responsive to determining that the set of estimated real-time glucose values are not within an acceptable accuracy range; or
controlling delivery of insulin by an insulin infusion device based on the set of estimated real-time glucose values responsive to determining that the set of estimated real-time glucose values are within the acceptable accuracy range.

20. The one or more non-transitory processor-readable media of claim 16, wherein the physiological model comprises a population-based model comprising one or more parameters weighted in accordance with one or more physiological parameters of a user.

* * * * *